(12) United States Patent
Kwang et al.

(10) Patent No.: US 8,298,684 B2
(45) Date of Patent: *Oct. 30, 2012

(54) PHENYLCARBAZOLE COMPOUNDS, ORGANIC LIGHT EMITTING DEVICE COMPRISING THE PHENYLCARBAZOLE COMPOUNDS AND FLAT PANEL DISPLAY DEVICE COMPRISING THE ORGANIC LIGHT EMITTING DEVICE

(75) Inventors: Seok-Hwan Kwang, Suwon-si (KR); Young-Kook Kim, Suwon-si (KR); Yoon-Hyun Kwak, Suwon-si (KR); Jeoung-In Yi, Suwon-si (KR); Hye-Lim Lee, Suwon-si (KR)

(73) Assignee: Samsung Display Co., Ltd. (KR)

( * ) Notice: Subject to any disclaimer, the term of this patent is extended or adjusted under 35 U.S.C. 154(b) by 461 days.

This patent is subject to a terminal disclaimer.

(21) Appl. No.: 12/322,017

(22) Filed: Jan. 27, 2009

(65) Prior Publication Data

US 2010/0032656 A1    Feb. 11, 2010

(30) Foreign Application Priority Data

May 20, 2008    (KR) .................. 10-2008-0046636

(51) Int. Cl.
 *H01L 51/54* (2006.01)
 *C07D 209/88* (2006.01)
(52) U.S. Cl. ........ 428/690; 428/917; 548/442; 313/504; 313/506; 257/40
(58) Field of Classification Search .................. None
See application file for complete search history.

(56) References Cited

U.S. PATENT DOCUMENTS

| 6,485,847 B1* | 11/2002 | Uchida et al. ............. 428/690 |
| 2006/0115680 A1* | 6/2006 | Hwang et al. ............. 428/690 |
| 2007/0231503 A1* | 10/2007 | Hwang et al. ............. 428/1.1 |
| 2009/0200928 A1* | 8/2009 | Hwang et al. ............. 313/504 |

FOREIGN PATENT DOCUMENTS

WO    WO 2008/010377 A1    1/2008

* cited by examiner

*Primary Examiner* — Dawn L. Garrett
(74) *Attorney, Agent, or Firm* — Knobbe Martens Olson & Bear LLP

(57) ABSTRACT

Provided are a compound represented by Formula 1 or 2 below and an organic light emitting device including an organic layer having the compound:

Formula 1

-continued

Formula 2

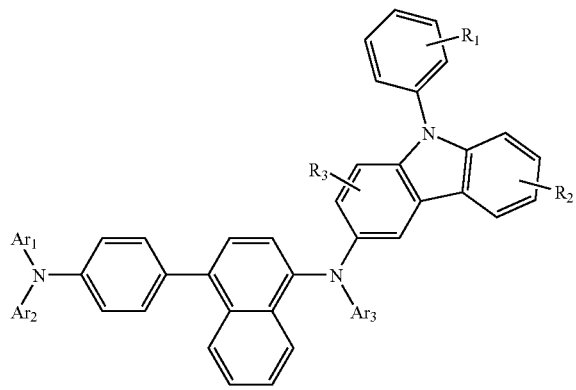

where $Ar_1$, $Ar_2$, $Ar_3$, $R_1$, $R_2$ and $R_3$ are as described in the detailed description. Since the compound represented by Formula 1 or 2 has excellent electrical properties and excellent charge transport capabilities, the compound can be efficiently used as a hole injecting material, a hole transporting material, and/or an emitting material which is suitable for a fluorescent or phosphorescent organic light emitting device which can realize all colors such as red, green, blue, and white. Thus, an OLED including the compound can have high efficiency, high current density, low driving voltage, excellent brightness, and long lifetime.

23 Claims, 2 Drawing Sheets

PHENYLCARBAZOLE COMPOUNDS, ORGANIC LIGHT EMITTING DEVICE COMPRISING THE PHENYLCARBAZOLE COMPOUNDS AND FLAT PANEL DISPLAY DEVICE COMPRISING THE ORGANIC LIGHT EMITTING DEVICE

CROSS-REFERENCE TO RELATED PATENT APPLICATION

This application claims the benefit of Korean Patent Application No. 10-2008-0046636, filed on May 20, 2008, in the Korean Intellectual Property Office, the disclosure of which is incorporated herein in its entirety by reference.

BACKGROUND OF THE INVENTION

1. Field of the Invention

The present embodiments relate to a phenylcarbazole compound, an organic light emitting device (OLED) including the phenylcarbazole compound, and a flat panel display device including the OLED, and more particularly, to a material having excellent electrical stability, excellent charge transporting properties, high glass transition temperature, and excellent crystallization prevention properties, an OLED including an organic layer having the material, and a flat panel display device including the OLED.

2. Description of the Related Art

Organic light emitting devices (OLEDs), which are self-emitting devices, have the advantages of having wide viewing angles, excellent contrast, and quick response times, and thus have drawn a large amount of public attention. In addition, OLEDs have low operating voltage, quick response times, and can realize full color display, and thus much research has been carried out on OLEDs.

Typically, an OLED has an anode/emission layer(EML)/cathode structure. Various other structures of OLEDs, such as an anode/hole transport layer (HTL)/EML/cathode structure and an anode/HTL/EML/electron injection layer (EIL)/cathode structure, can be obtained by interposing layers such as a hole injection layer (HIL), HTL, and EIL at various positions between the anode and the EML or between the EML and the cathode.

It is known to use a polyphenyl compound or an anthracene derivative to form a HTL (U.S. Pat. Nos. 6,596,415 and 6,465,115). However, lifetime, efficiency, and power consumption characteristics of OLEDs formed of materials conventionally used to form a HIL and/or a HTL do not meet desired levels. Accordingly, there is a need to improve those characteristics. The present embodiments below overcome the problems described above as well as provide additional advantages.

SUMMARY OF THE INVENTION

The present embodiments provide a material having excellent electrical stability, excellent charge transporting properties, high glass transition temperature, and excellent crystallization prevention properties, wherein the material is used to form an organic layer suitable for a fluorescent or phosphorescent organic light emitting device (OLED) which can realize all colors such as red, green, blue, and white. In addition, the present embodiments also provide an OLED having high efficiency, low driving voltage, and excellent brightness by including the organic layer, and a flat panel display device including the OLED.

According to an aspect of the present embodiments, there is provided a compound represented by Formula 1 or 2 below:

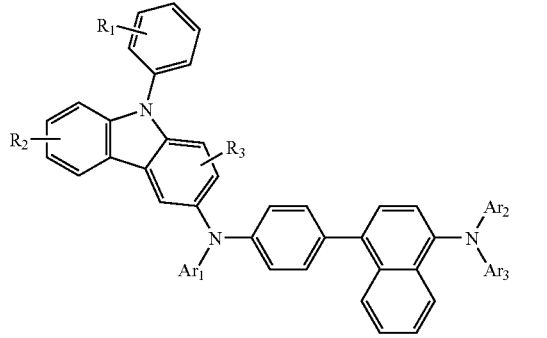

where $Ar_1$, $Ar_2$ and $Ar_3$ are each independently a substituted or unsubstituted $C_6$-$C_{20}$ aryl group, a substituted or unsubstituted $C_6$-$C_{20}$ aryloxy group, a substituted or unsubstituted $C_4$-$C_{20}$ heteroaryl group, or a substituted or unsubstituted $C_4$-$C_{20}$ polycyclic condensed ring, and $R_1$, $R_2$ and $R_3$ are each independently a hydrogen atom, a substituted or unsubstituted C1-C10 alkyl group, a substituted or unsubstituted C1-C10 alkoxy group, a fluorine atom, a cyano group, or an amine group, wherein two or more of $R_1$, $R_2$, and $R_3$ can be bound with one another to form a saturated or unsaturated carbon ring.

According to another aspect of the present embodiments, there is provided an organic light emitting device comprising: a first electrode; a second electrode; and an organic layer including the compound represented by Formula 1 or 2 interposed between the first electrode and the second electrode.

The organic layer may be a hole injection layer, a hole transport layer, or an emission layer.

According to another aspect of the present embodiments, there is provided a flat panel display device comprising the organic light emitting device, wherein the first electrode of the organic light emitting device is electrically connected to a source electrode or a drain electrode of a thin film transistor.

BRIEF DESCRIPTION OF THE DRAWINGS

The above and other features and advantages of the present embodiments will become more apparent by describing in detail exemplary embodiments thereof with reference to the attached drawings in which.

DETAILED DESCRIPTION OF THE INVENTION

Figure 1:
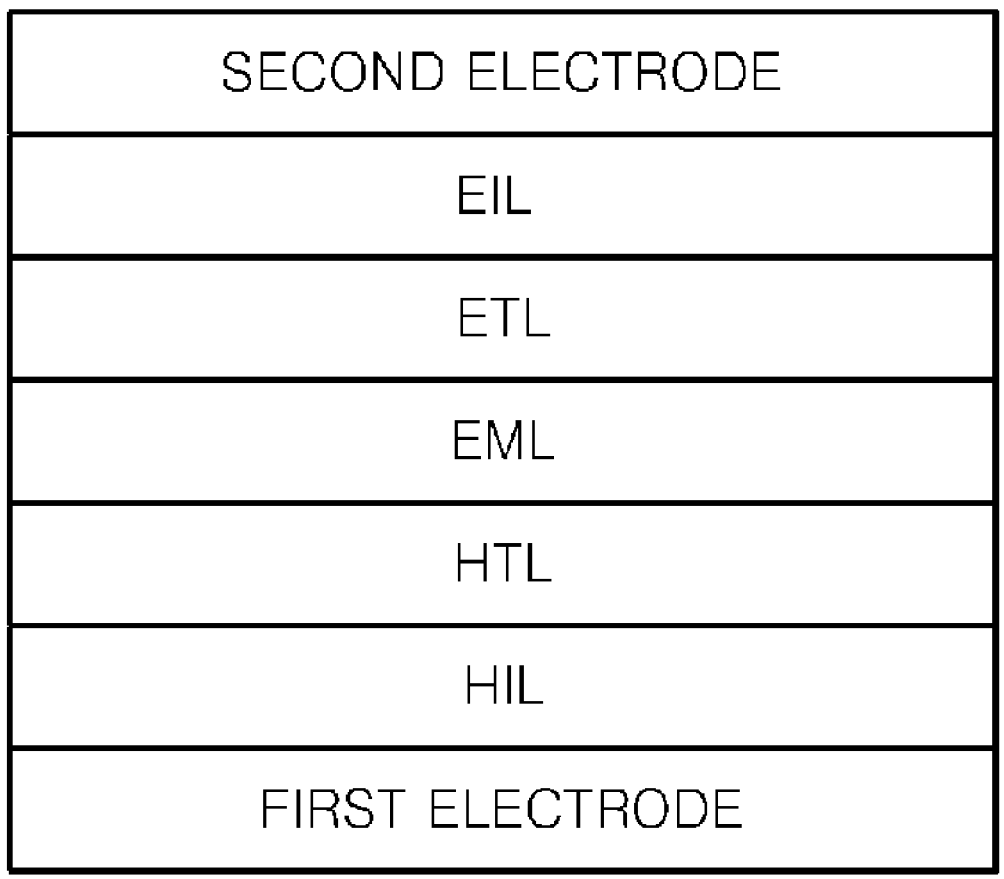
FIG. 1 shows a structure of an OLED according to an embodiment.

Hereinafter, the present embodiments will be described more fully with reference to the accompanying drawings, in which exemplary embodiments are shown.

Some embodiments relate to a compound represented by Formula 1 or 2 below:

Formula 1

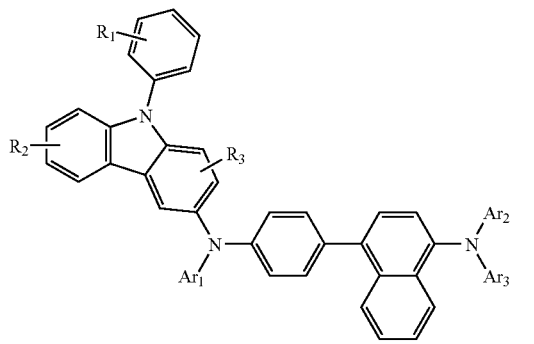

Formula 2

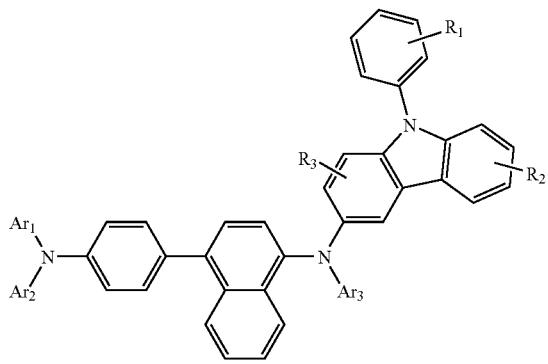

wherein $Ar_1$, $Ar_2$ and $Ar_3$ are each independently a substituted or unsubstituted $C_6$-$C_{20}$ aryl group, a substituted or unsubstituted $C_6$-$C_{20}$ aryloxy group, a substituted or unsubstituted $C_4$-$C_{20}$ heteroaryl group, or a substituted or unsubstituted $C_4$-$C_{20}$ polycyclic condensed ring, $R_1$, $R_2$ and $R_3$ are each independently a hydrogen atom, a substituted or unsubstituted $C_1$-$C_{10}$ alkyl group, a substituted or unsubstituted $C_1$-$C_{10}$ alkoxy group, a fluorine atom, a cyano group, or an amine group, wherein two or more of $R_1$, $R_2$, and $R_3$ can be bound with one another to form a saturated or unsaturated carbon ring.

The compound represented by Formula 1 or 2 according to the present embodiments may be used as a hole injecting material, a hole transporting material and/or an emitting material. In some embodiments, the compounds of Formula 1 or 2 have at least one phenylcarbazole structure, and thus the glass transition temperature (Tg) or the melting point of the compound increases. Thus, during the operation of the OLED, the compound is highly resistant to heat generated in an organic layer, between organic layers or between an organic layer and a metal electrode according to Joule's Law, and is stable in a high temperature environment. If the phenylcarbazole compound according to the present embodiments is used to form an OLED, excellent durability can be obtained both when the OLED is stored and operated.

In the compound of Formula 1 or 2, $Ar_1$ and $Ar_2$ may each independently be a substituted or unsubstituted $C_6$-$C_{20}$ aryl group, or a substituted or unsubstituted $C_4$-$C_{20}$ heteroaryl group.

$Ar_1$, $Ar_2$ and $Ar_3$ may also each independently be a phenyl group, a $C_1$-$C_5$ alkylphenyl group, a $C_1$-$C_5$ alkoxyphenyl group, a cyanophenyl group, a phenoxyphenyl group, a fluorophenyl group, a naphthyl group, a $C_1$-$C_5$ alkylnaphthyl group, a $C_1$-$C_5$ alkoxynaphthyl group, a cyanonaphthyl group, a halonaphthyl group, a fluorenyl group, a carbazolyl group, a $C_1$-$C_5$ alkyl carbazolyl group, a biphenyl group, a $C_1$-$C_5$ alkyl biphenyl group, a $C_1$-$C_5$ alkoxy biphenyl group, or a pyridyl group.

$Ar_1$, $Ar_2$ or $Ar_3$ may also be a phenyl group, a methyl phenyl group, a methyl biphenyl group, an ethyl phenyl group, an ethyl biphenyl group, an o-, m- or p-fluorophenyl group, a dichlorophenyl group, a cyanophenyl group, a dicyanophenyl group, a trifluorophenyl group, a methoxyphenyl group, an o-, m- or p-tolyl group, a mesityl group, a phenoxyphenyl group, an (α,α-dimethylbenzene) a phenyl group, an (N,N'-dimethyl)aminophenyl group, an (N,N'-diphenyl)aminophenyl group, a pentalenyl group, a naphthyl group, a methyl naphthyl group, an anthracenyl group, an azulenyl group, a heptalenyl group, an acenaphthylenyl group, a fluorenyl group, an anthraquinolyl group, a phenanthryl group, a triphenylene group, a pentaphenyl group, a hexaphenyl group, a carbazolyl group, or the like.

$Ar_1$, $Ar_2$ and $Ar_3$ may also each independently be a monocyclic, bicyclic or tricyclic aryl group such as a fluorenyl group, a carbazolyl group, a phenyl group, a naphthyl group, and a biphenyl group, or the aryl group having aromatic rings substituted with 1-3 substituents selected from the group consisting of a $C_1$-$C_4$ alkyl group, a $C_1$-$C_5$ alkoxy group, a cyano group, an amine group, a phenoxy group, a phenyl group and a halogen atom.

Non-limiting examples of the unsubstituted alkyl group used herein include a methyl group, an ethyl group, a propyl group, an isobutyl group, a sec-butyl group, a tert-butyl group, a pentyl group, an iso-amyl group, and a hexyl group, wherein at least one hydrogen atom of the alkyl group may be substituted with a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkenyl group, a $C_1$-$C_{10}$ alkynyl group, a $C_6$-$C_{20}$ aryl group, a $C_7$-$C_{20}$ arylalkyl group, a $C_4$-$C_{20}$ heteroaryl group, or a $C_5$-$C_{20}$ hetoroarylalkyl group.

Non-limiting examples of the unsubstituted alkoxy group used herein include a methoxy group, an ethoxy group, a phenyloxy group, a cyclohexyloxy group, a naphthyloxy group, and a diphenyloxy group, wherein at least one hydrogen atom of the alkoxy group may be substituted with a substituent described above with reference to the alkyl group.

In some embodiments, the unsubstituted aryl group used herein is used alone or in combination, and is a carbocyclic aromatic system including at least one ring. The rings may be attached to each other or fused with each other using a pendent method. At least one hydrogen atom of the aryl group may be substituted with a substituent described above with reference to the alkyl group.

Non-limiting examples of the unsubstituted aryloxy group used herein include a phenyloxy group, a naphthyleneoxy group, and a diphenyloxy group. At least one hydrogen atom of the aryloxy group may be substituted with a substituent described above with reference to the alkyl group.

The unsubstituted heteroaryl group used herein is a monovalent monocyclic or bivalent bicyclic organic compound that includes 1, 2 or 3 hetero atoms selected from N, O, P or S and includes a ring composed of 4 to 20 carbon atoms.

At least one hydrogen atom of the heteroaryl group may be substituted with a substituent described above with reference to the alkyl group.

Non-limiting examples of the heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, and an indolyl group.

The compounds represented by Formula 1 or 2 may be one of the Compounds 1 to 126 represented by Formula 7. However, the compounds of Formula 1 or 2 is not limited thereto.

Formula 7

1

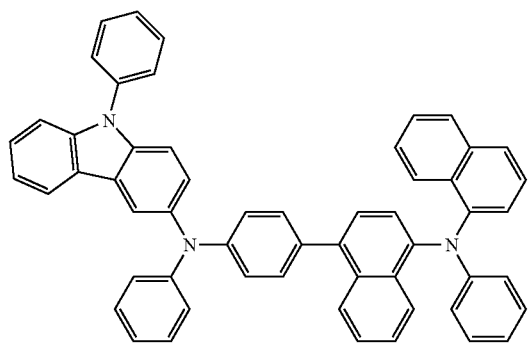

2

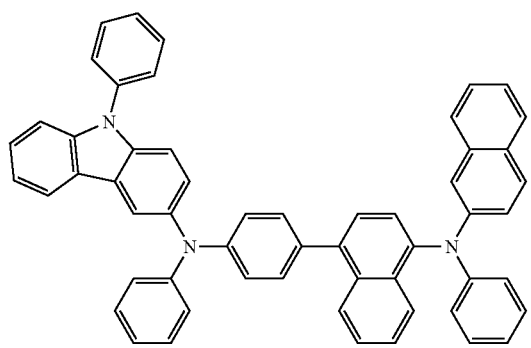

3

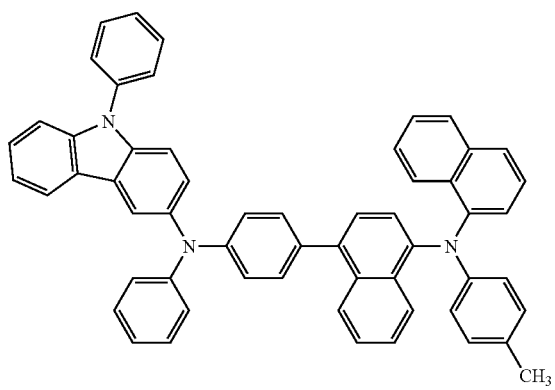

4

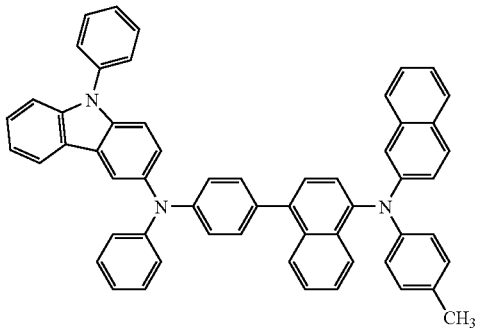

5

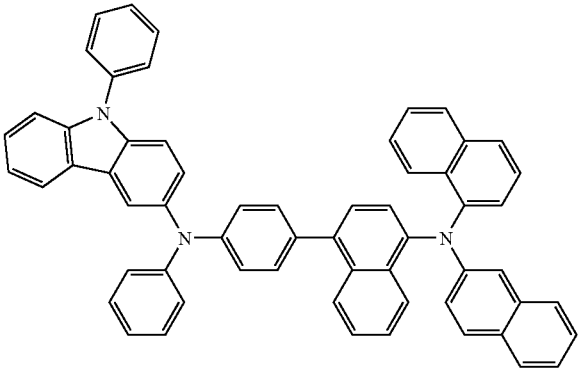

6

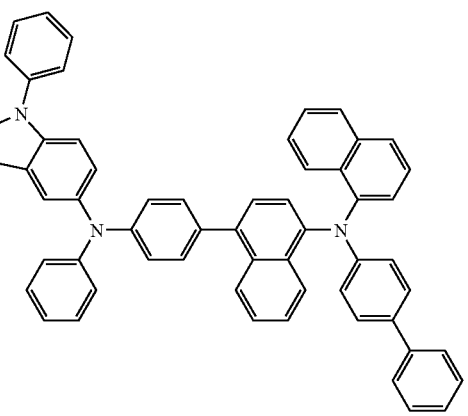

7

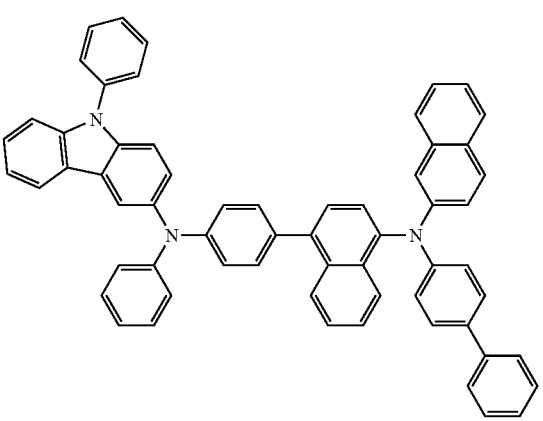

8
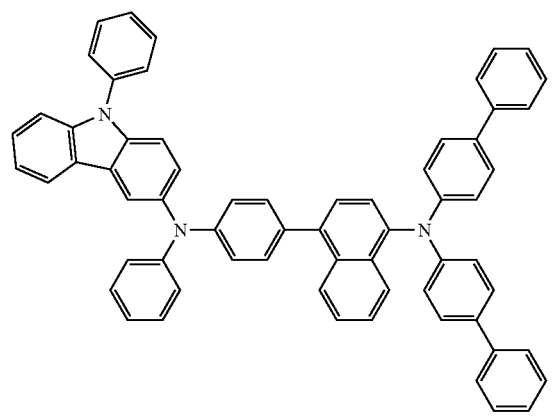
9
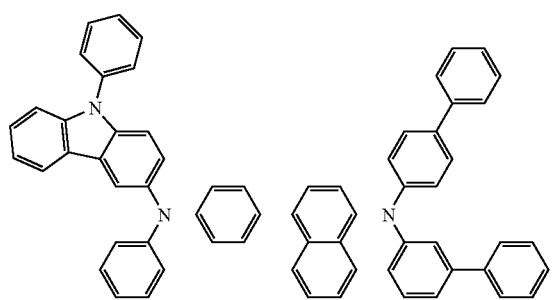
10
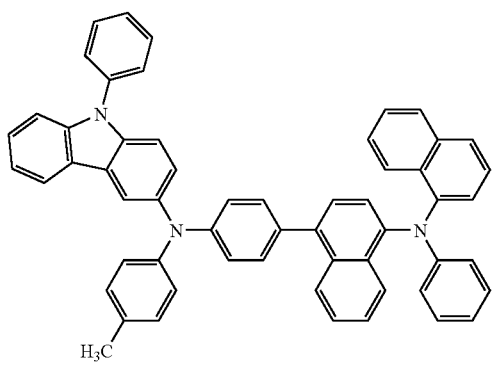
11
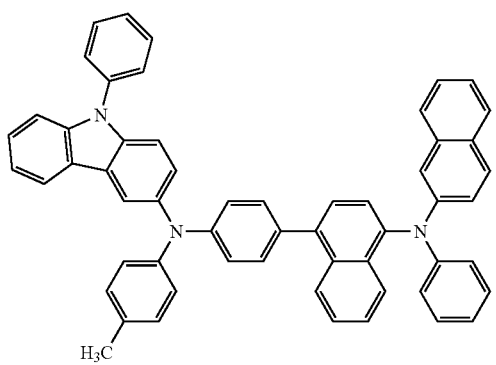
12
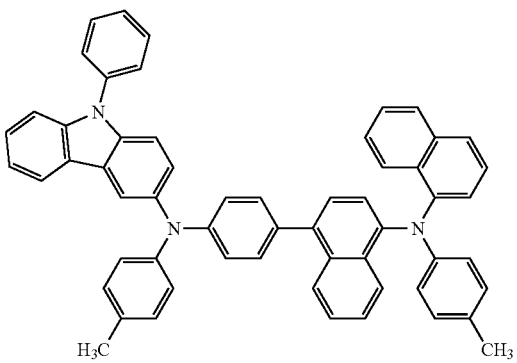
13
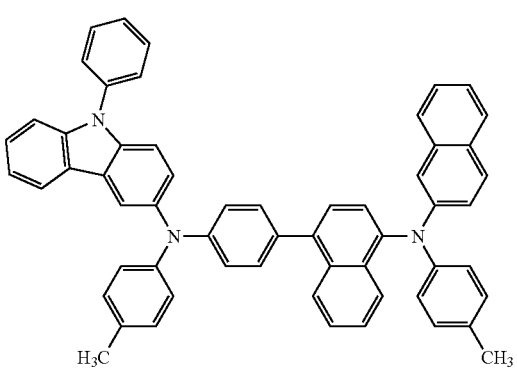
14
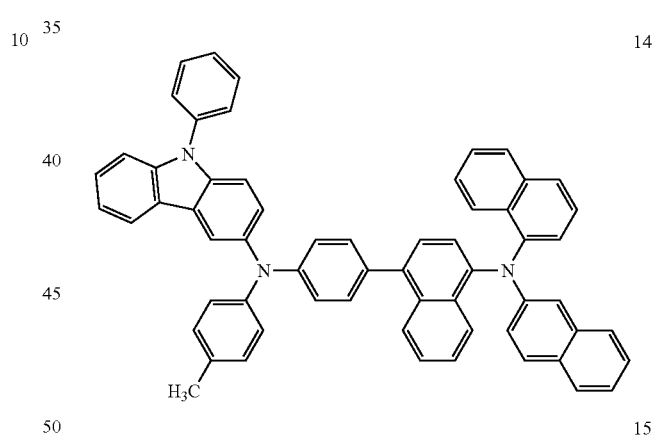
15
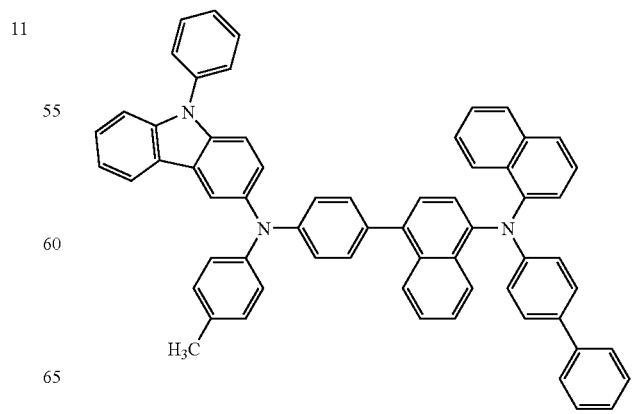

16
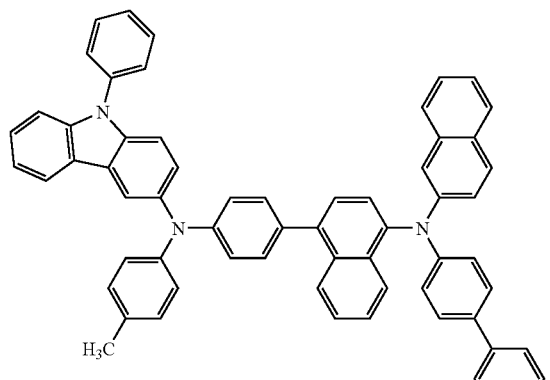
17
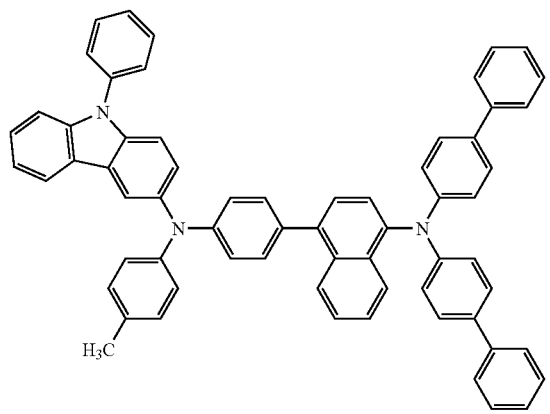
18
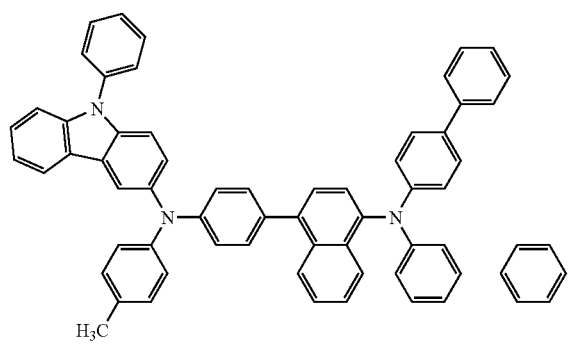
19
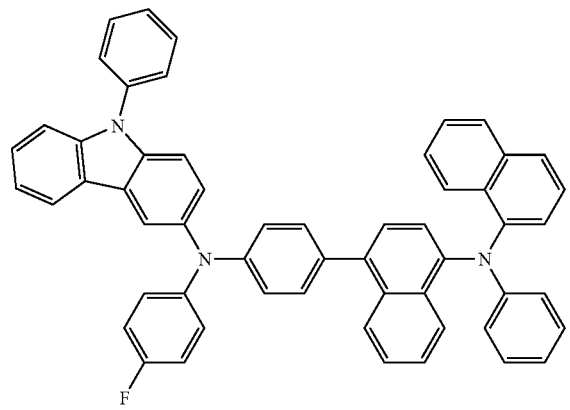
20
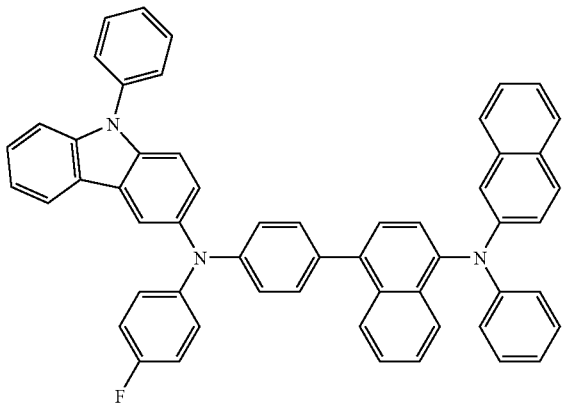
21
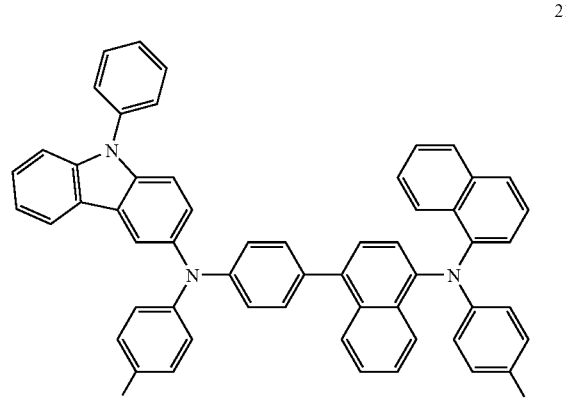
22
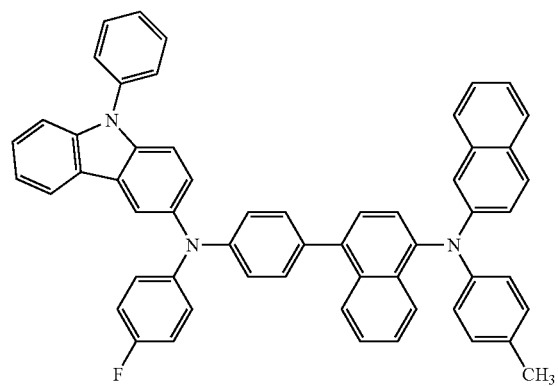
23
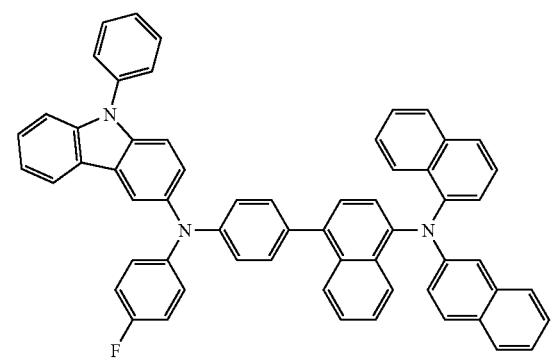

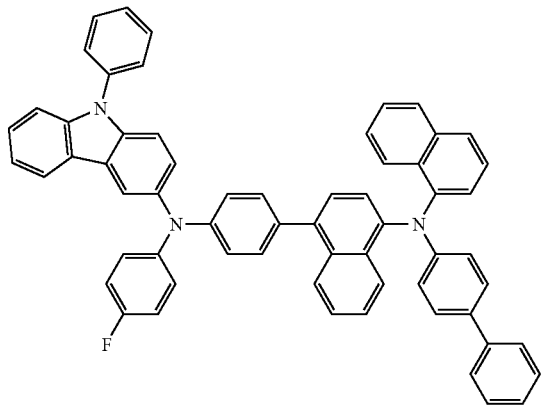
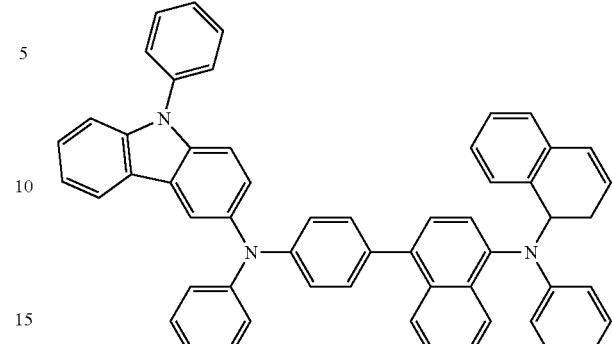
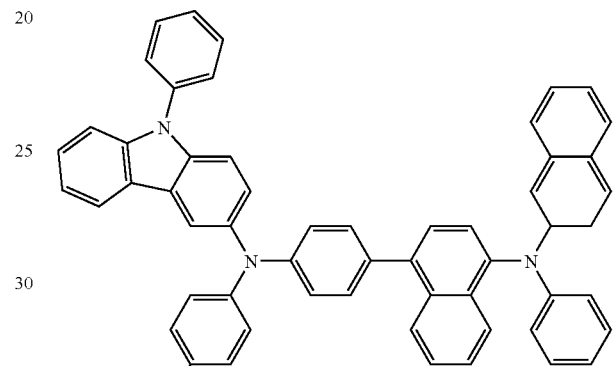
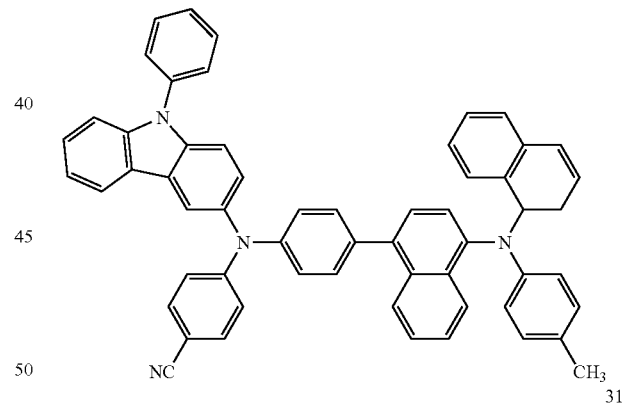
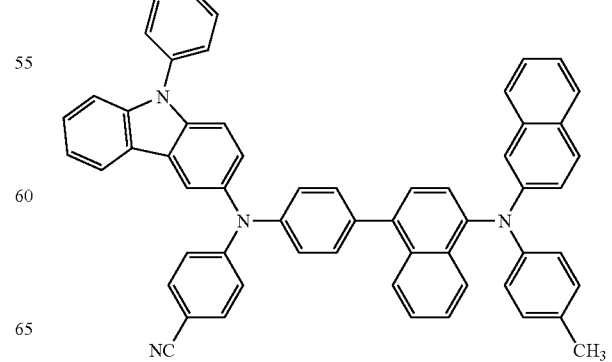

32
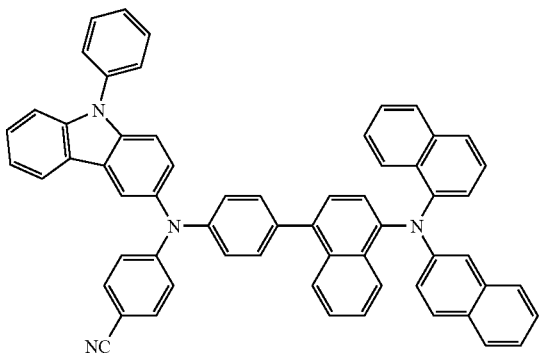
33
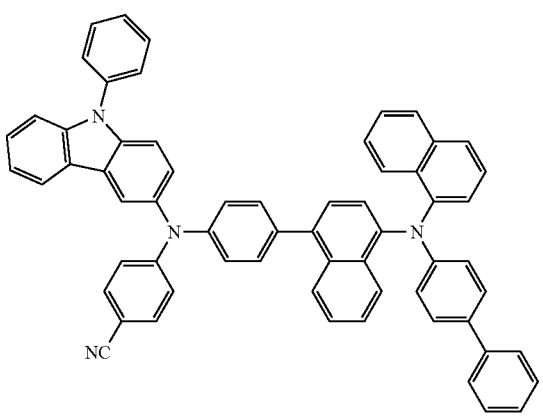
34
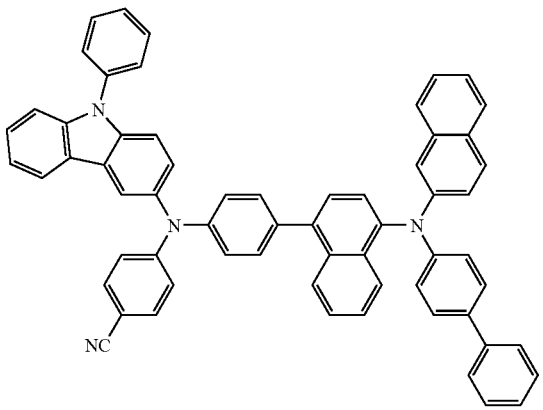
35
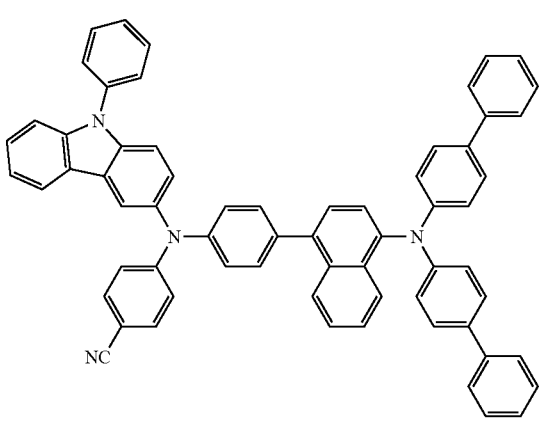
36
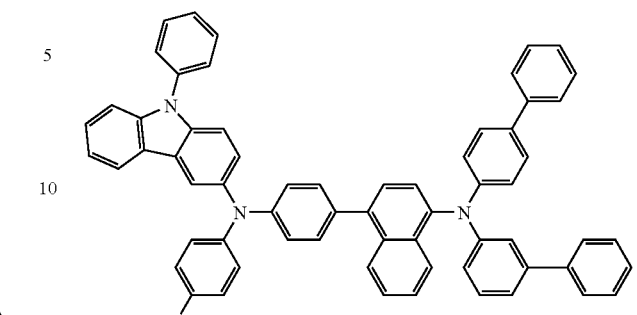
37
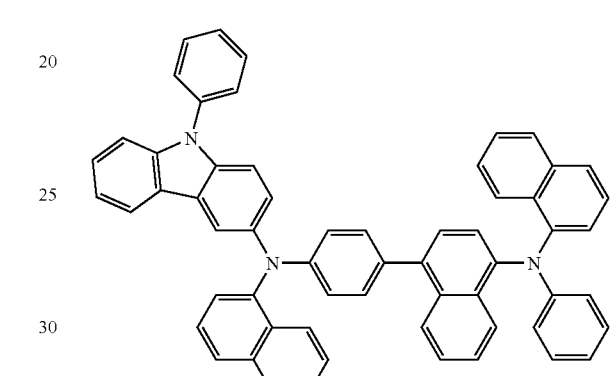
38
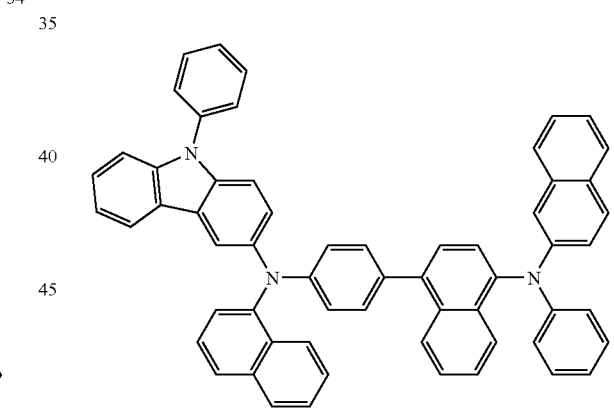
39
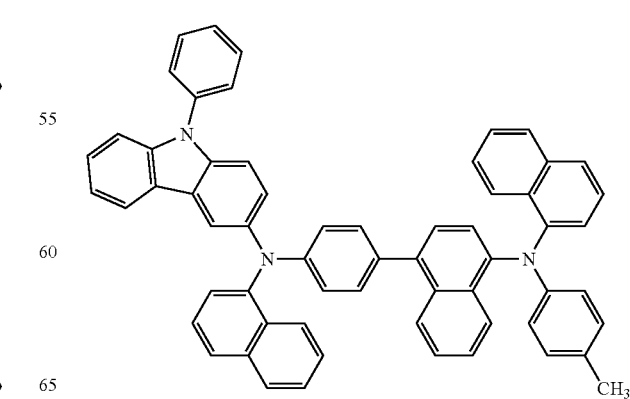

40
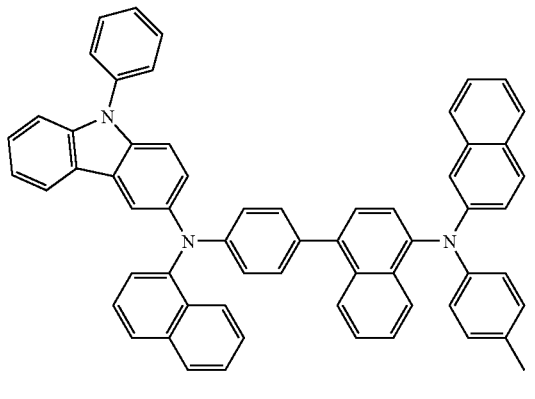
41
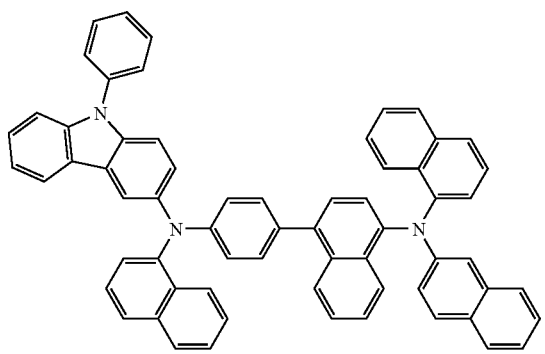
42
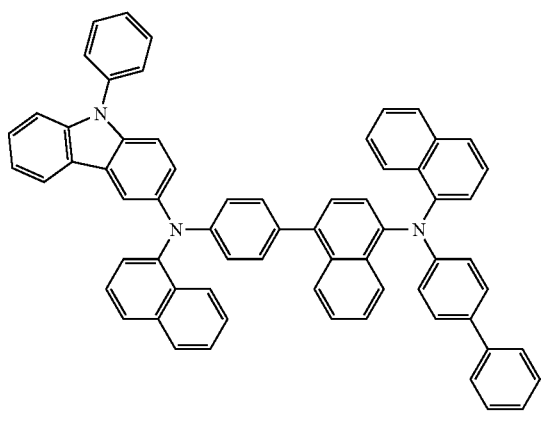
43
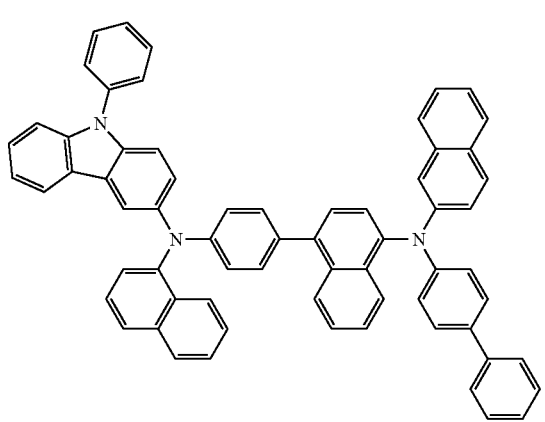
44
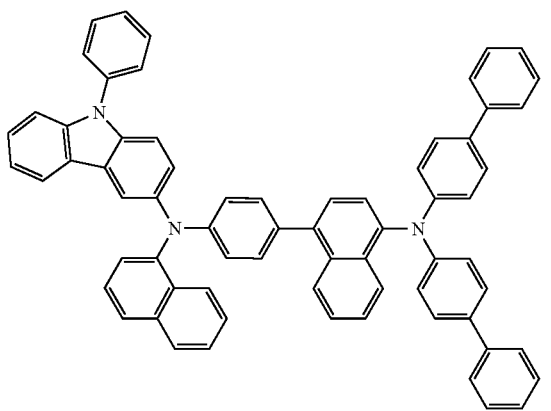
45
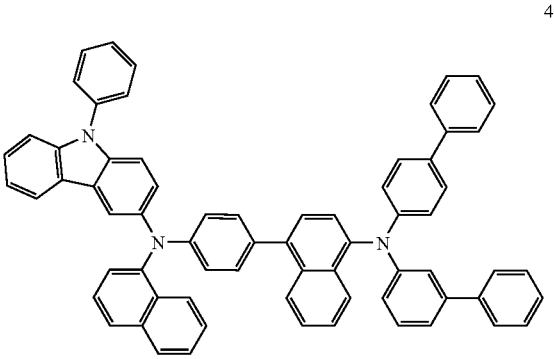
46
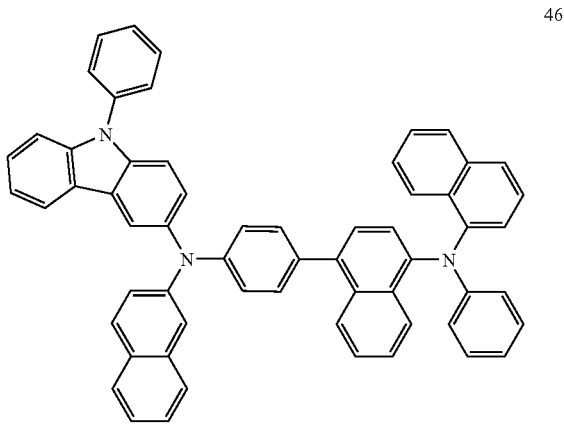
47
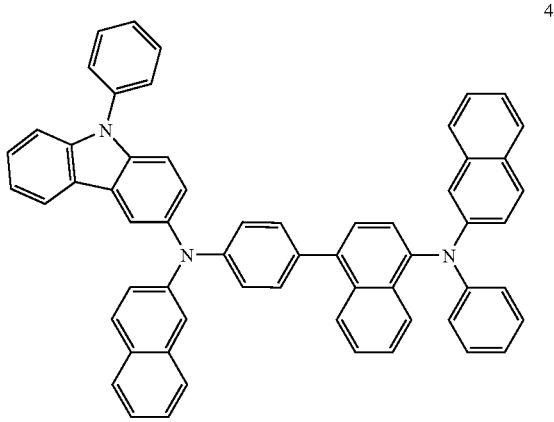

48
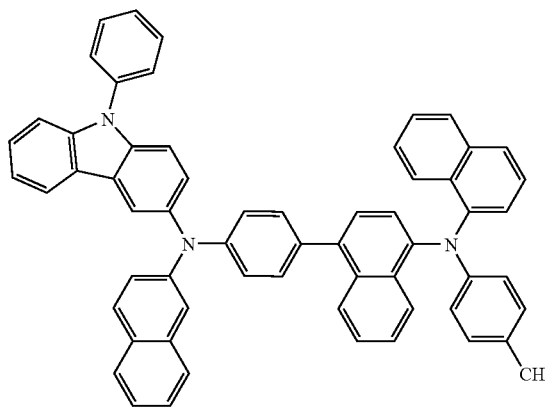
49
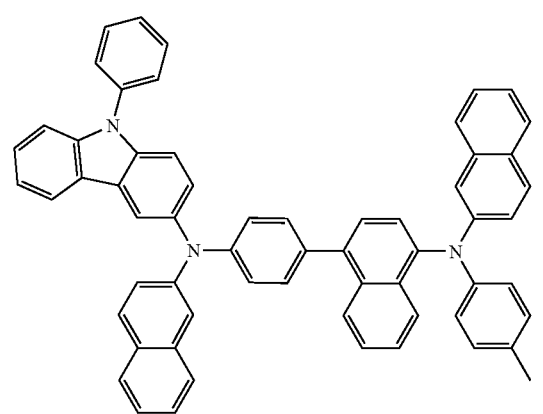
50
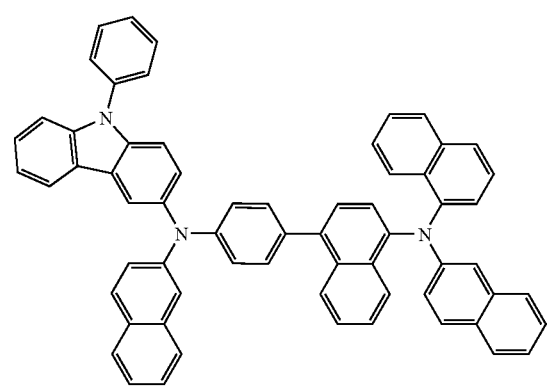
51
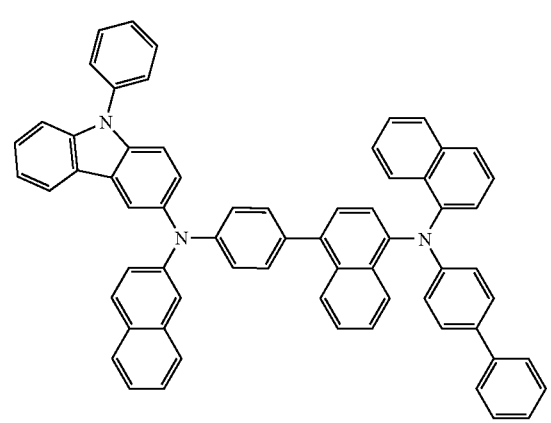
52
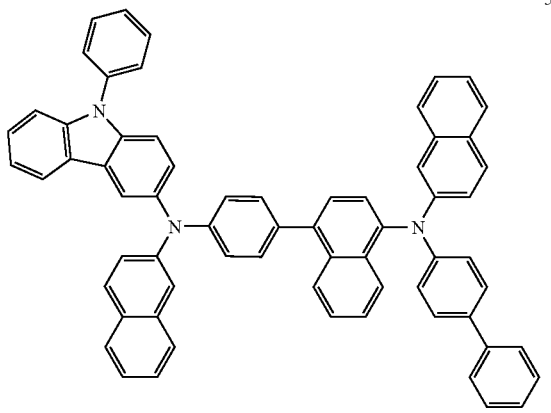
53
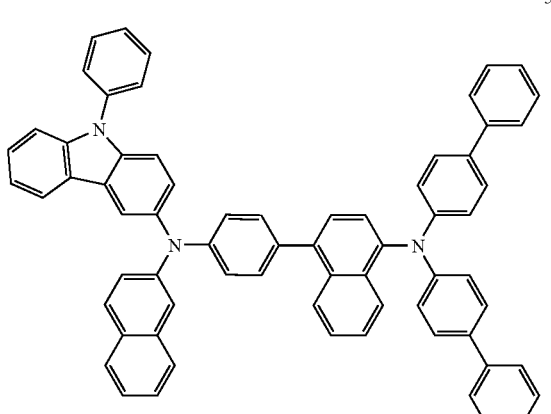
54
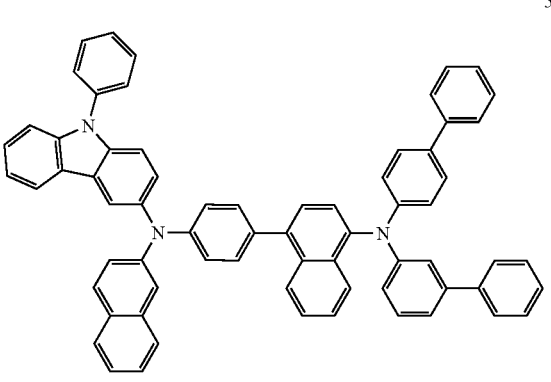
55
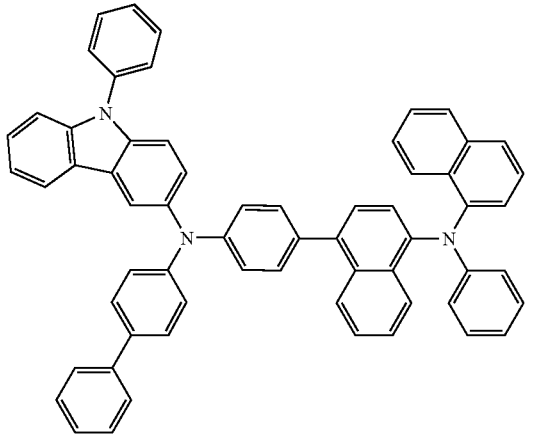

-continued
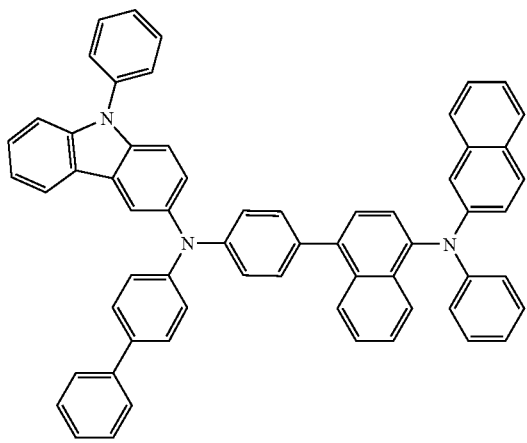
56
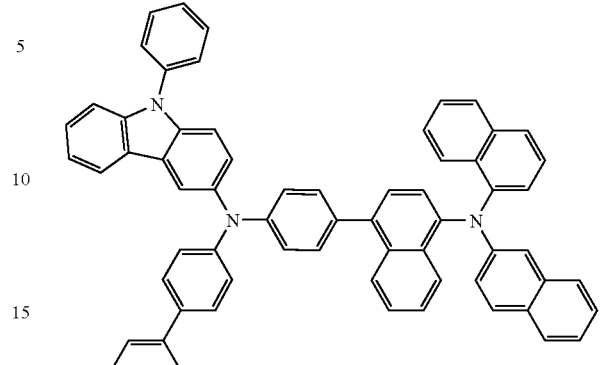
59
57
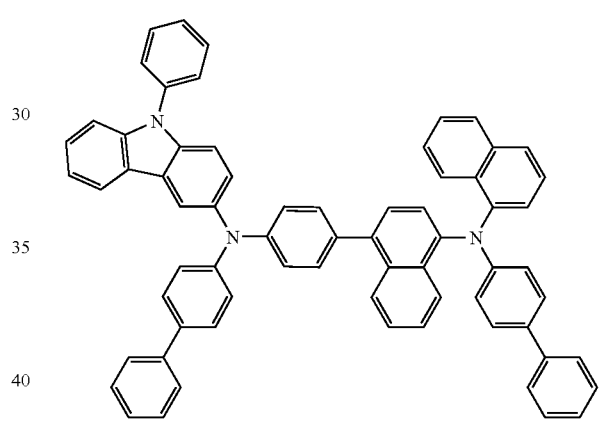
60
58
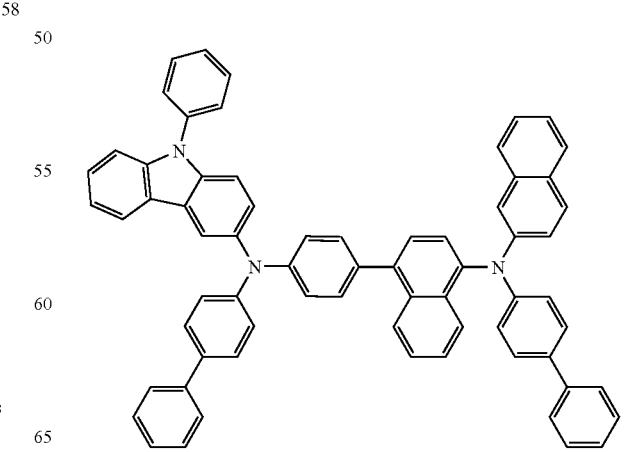
61

62
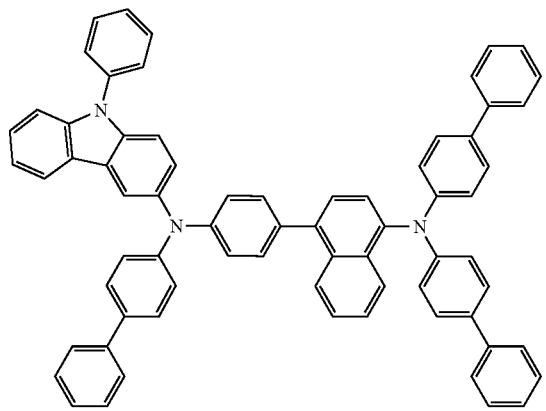
63
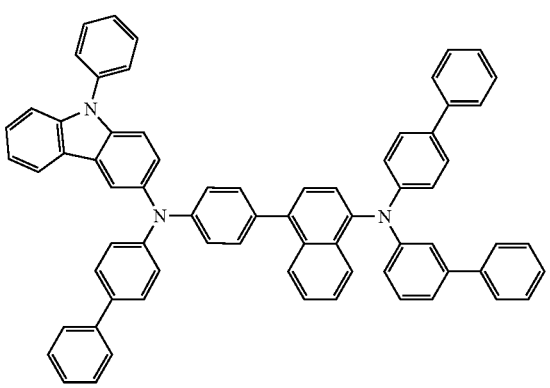
64
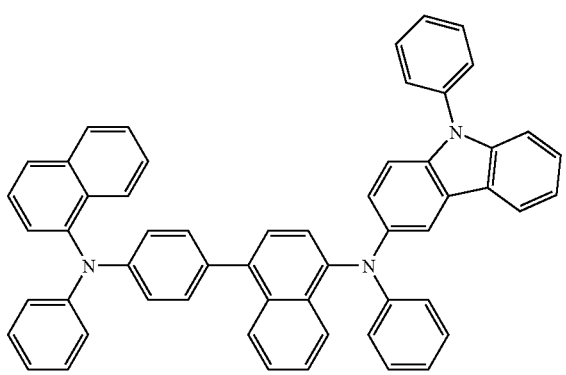
65
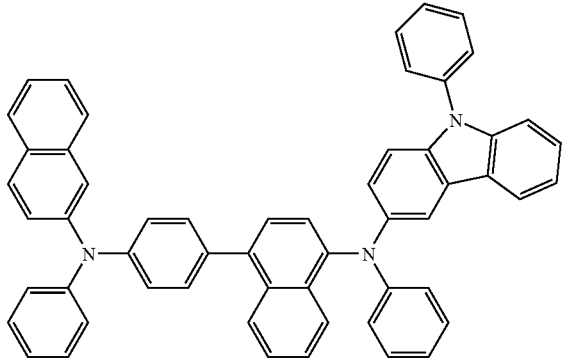
66
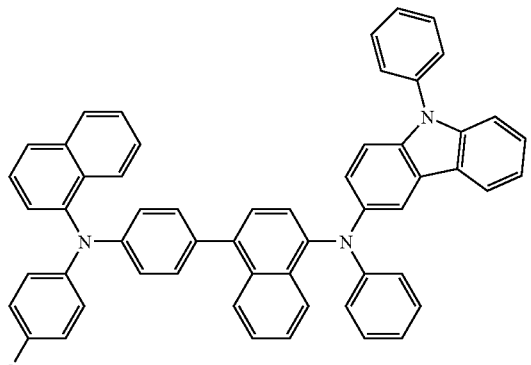
67
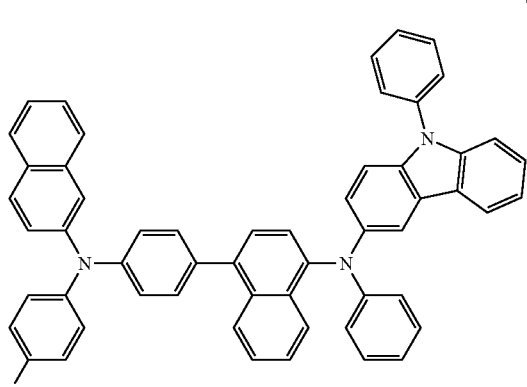
68
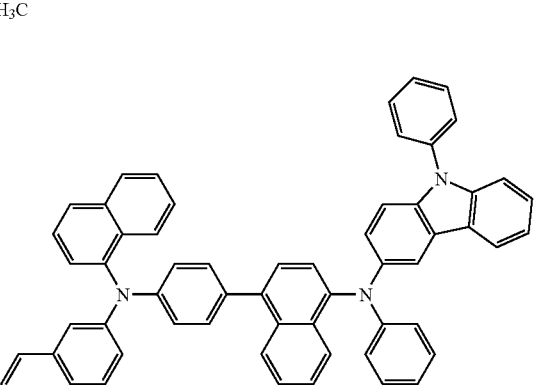
69
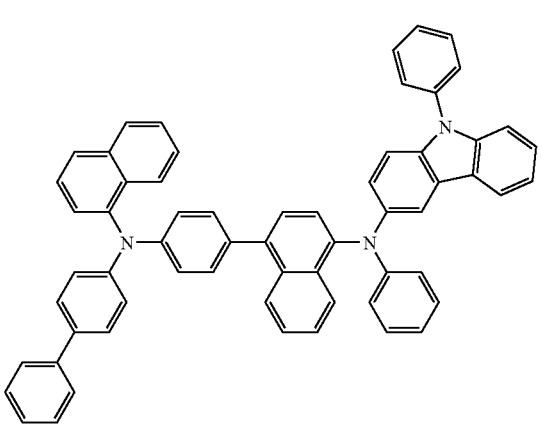

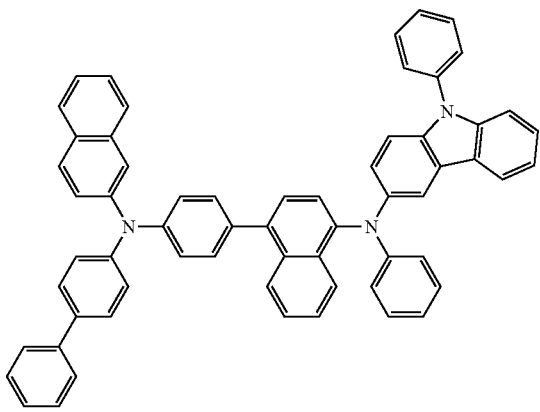
70
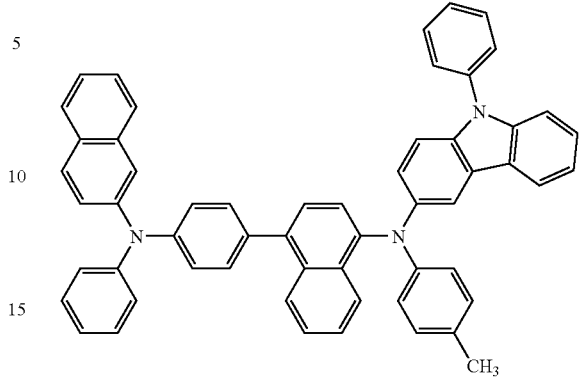
74
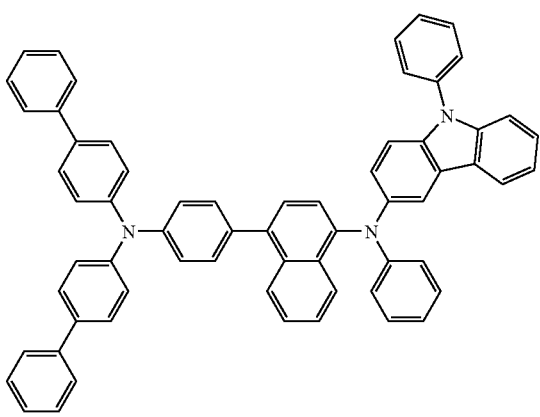
71
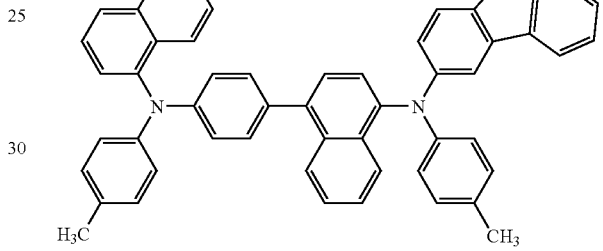
75
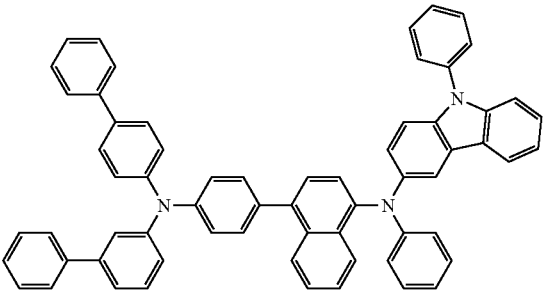
72
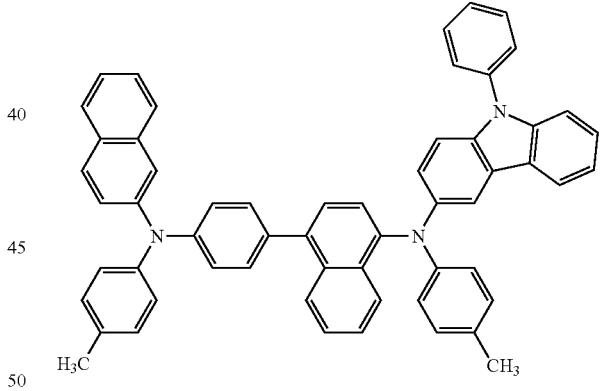
76
73
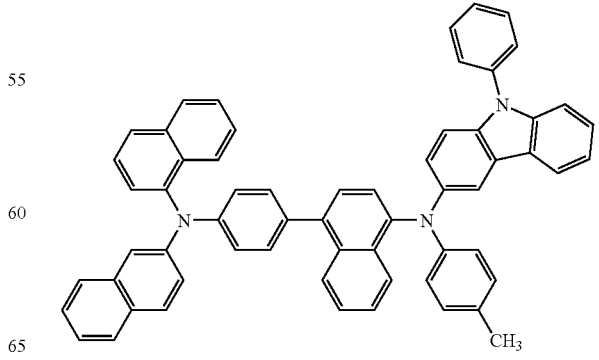
77

-continued
78
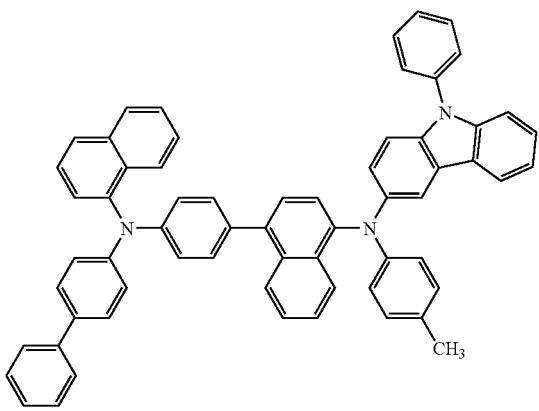
79
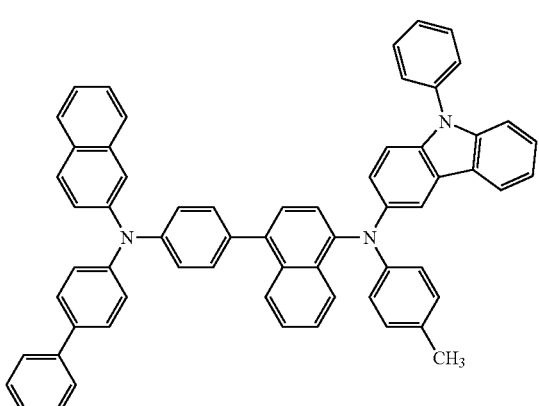
80
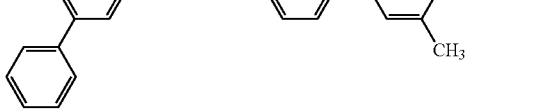
81
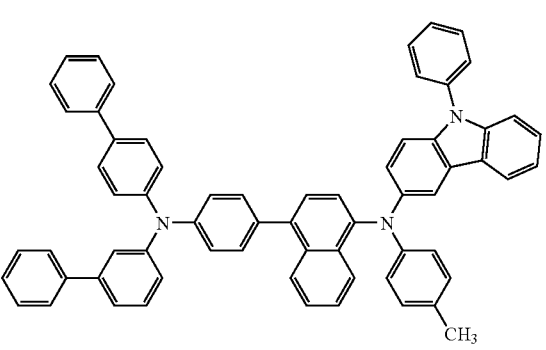
-continued
82
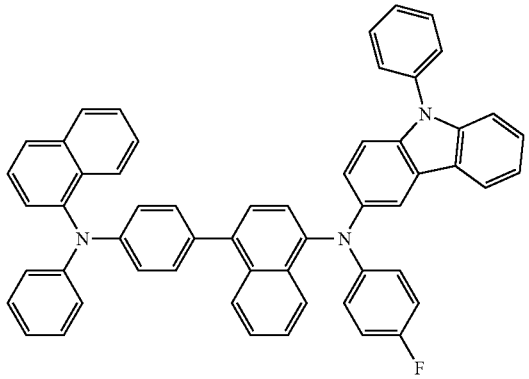
83
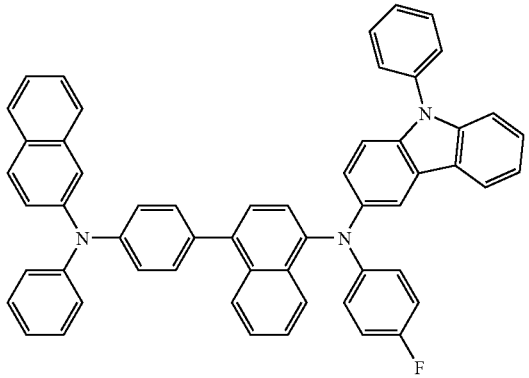
84
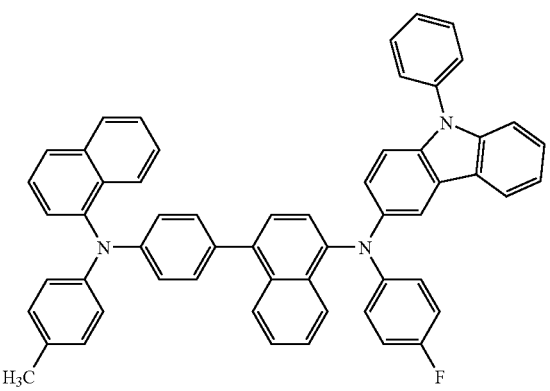
85
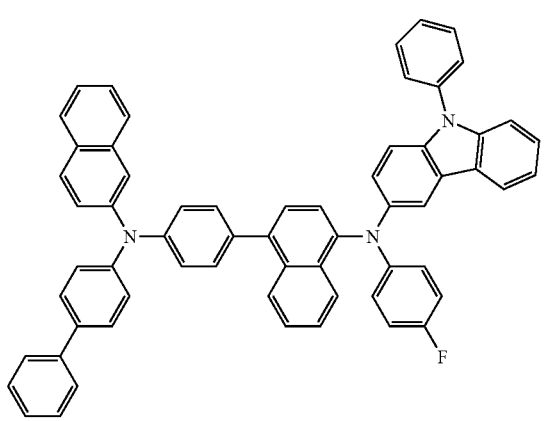

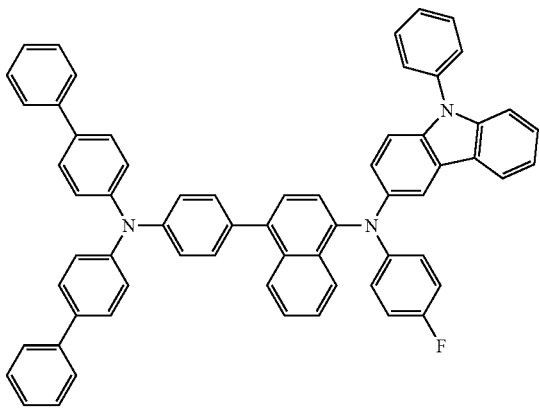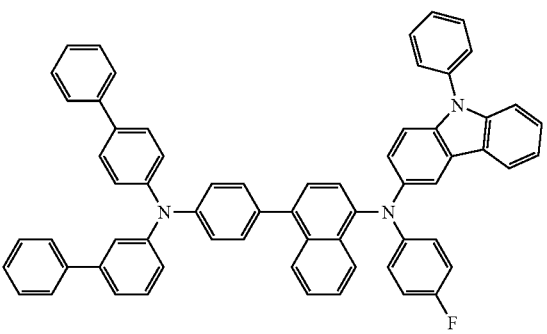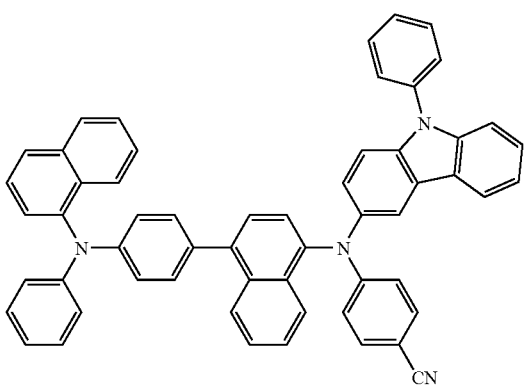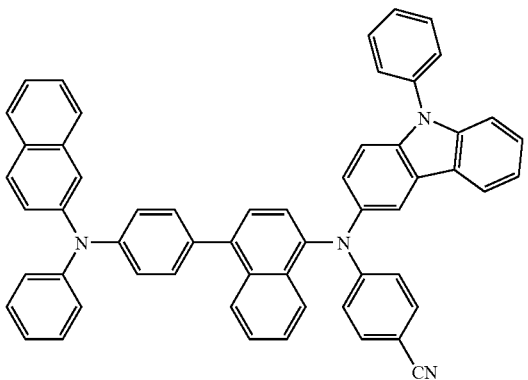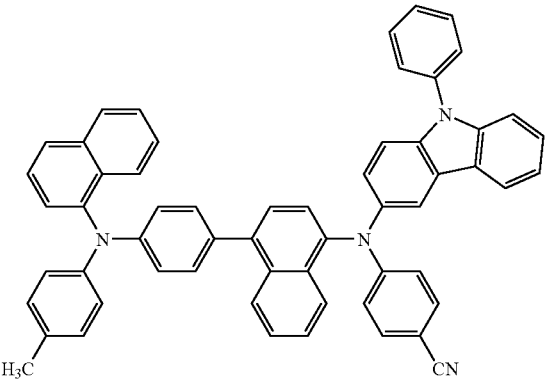

94
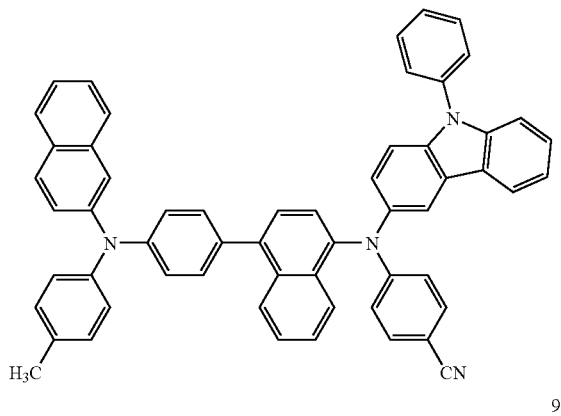
95
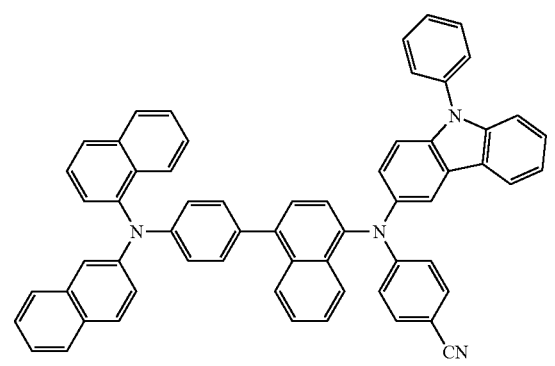
96
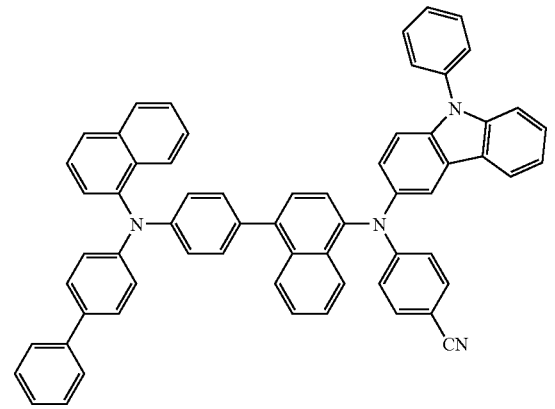
97
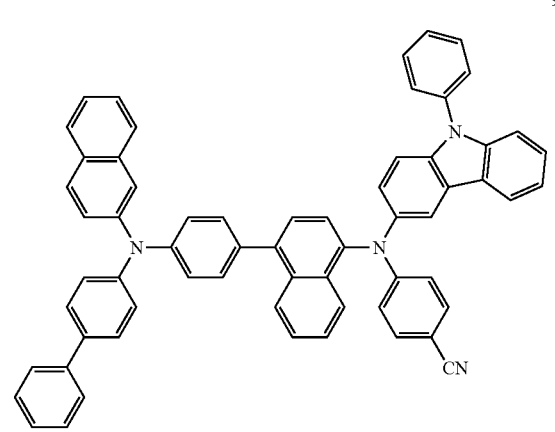
98
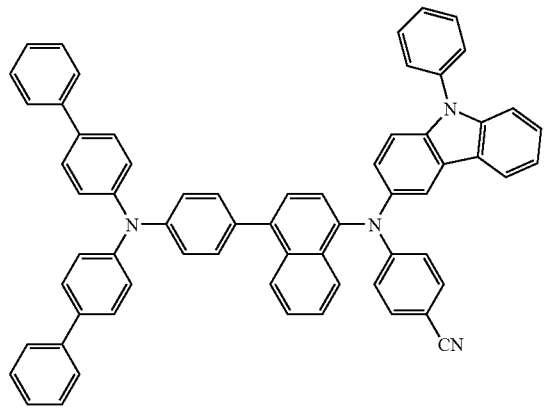
99
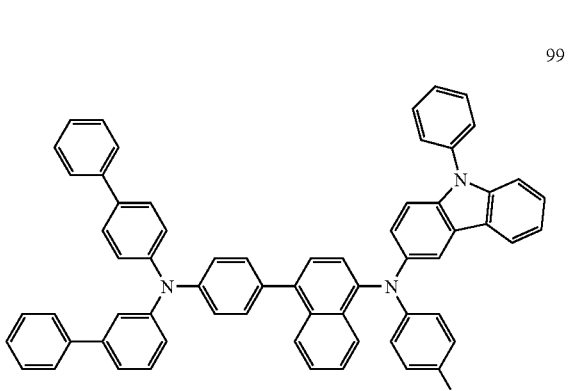
100
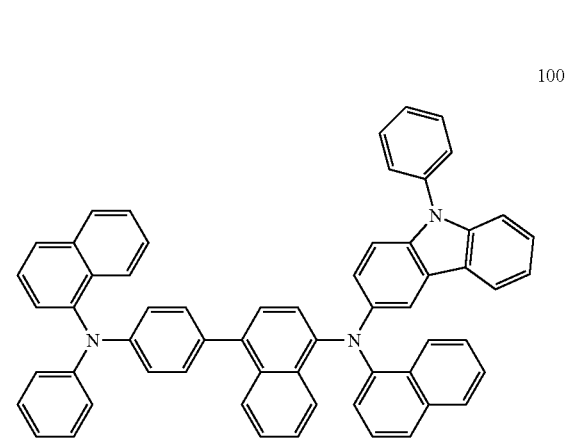
101
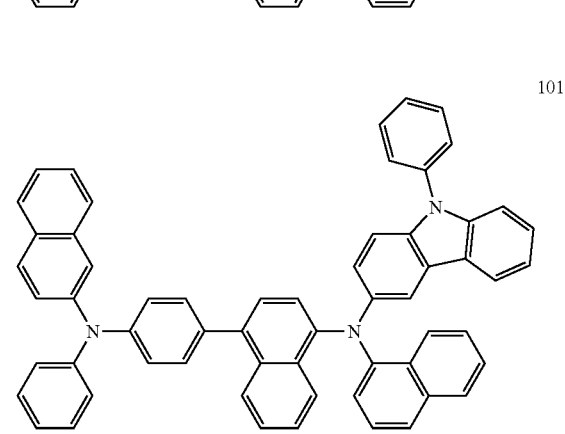

102
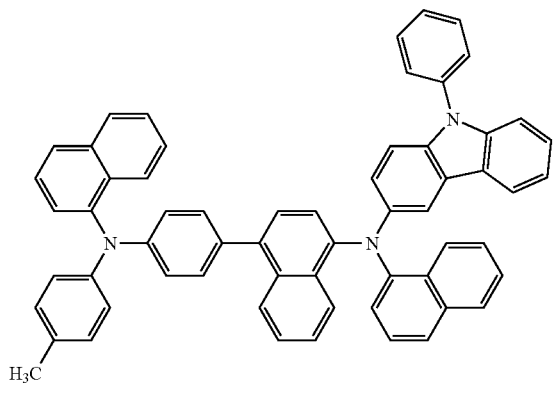
103
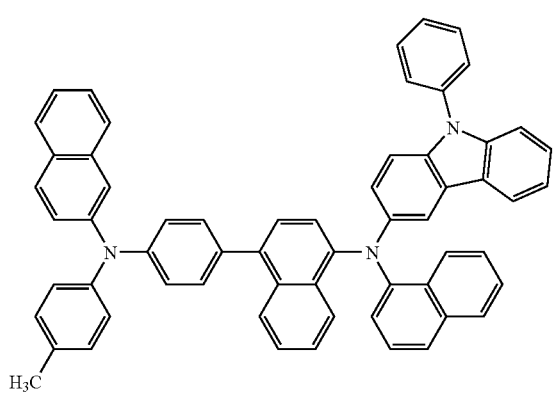
104
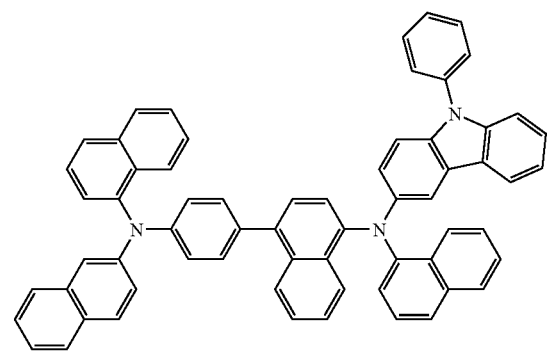
105
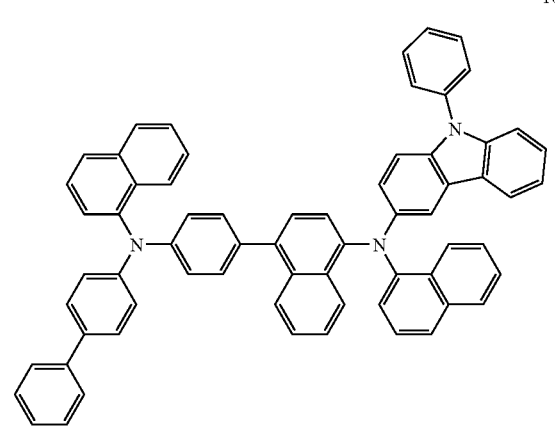
106
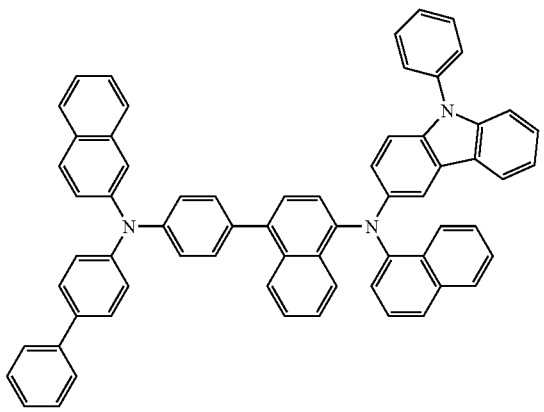
107
108
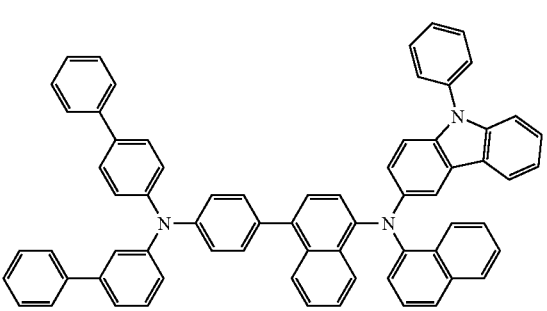
109
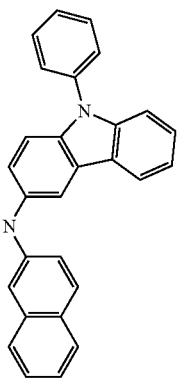

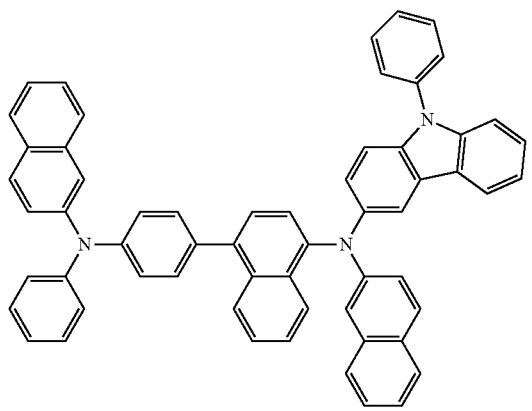
110
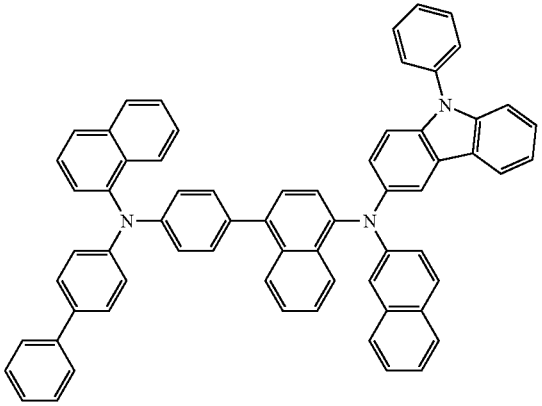
114
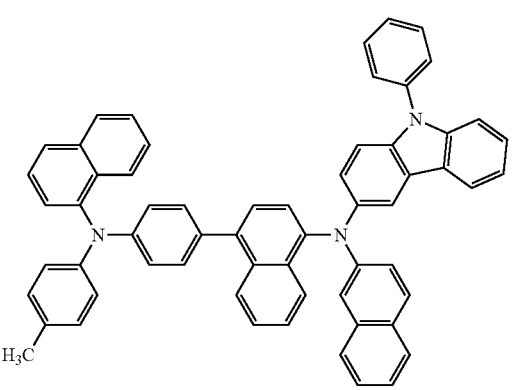
111
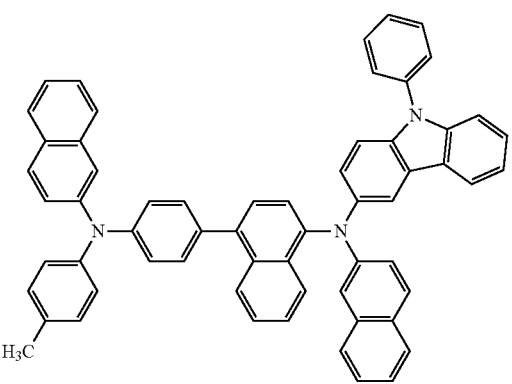
112
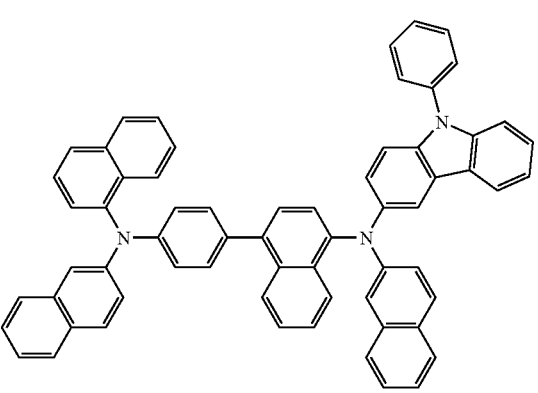
113
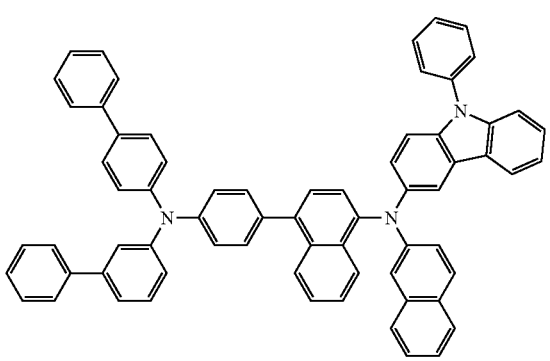

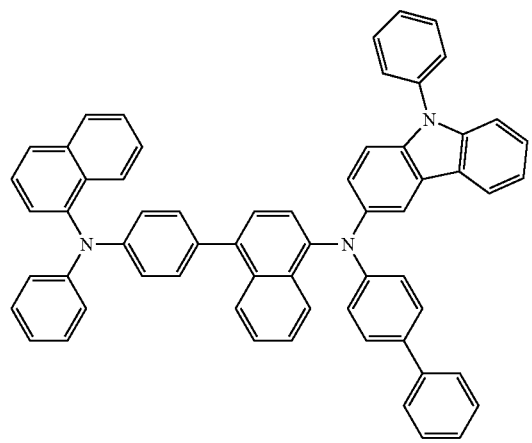
118
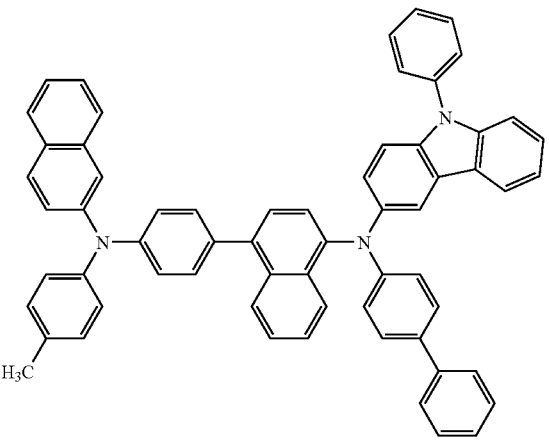
121
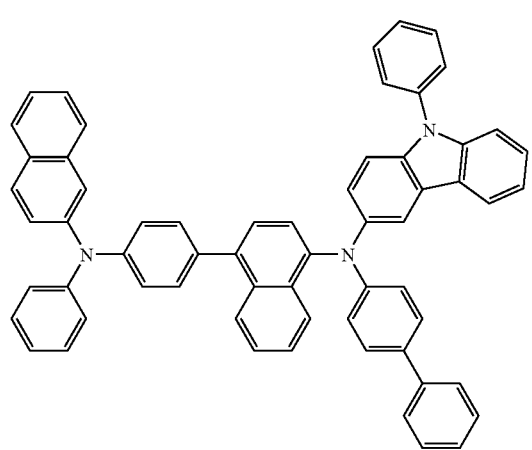
119
122
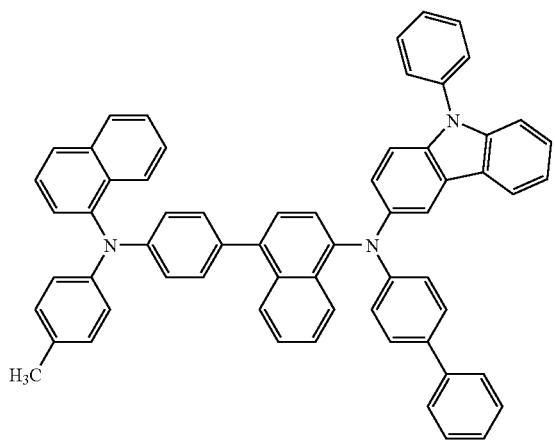
120
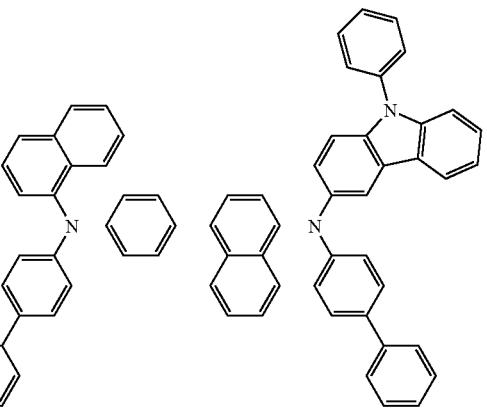
123

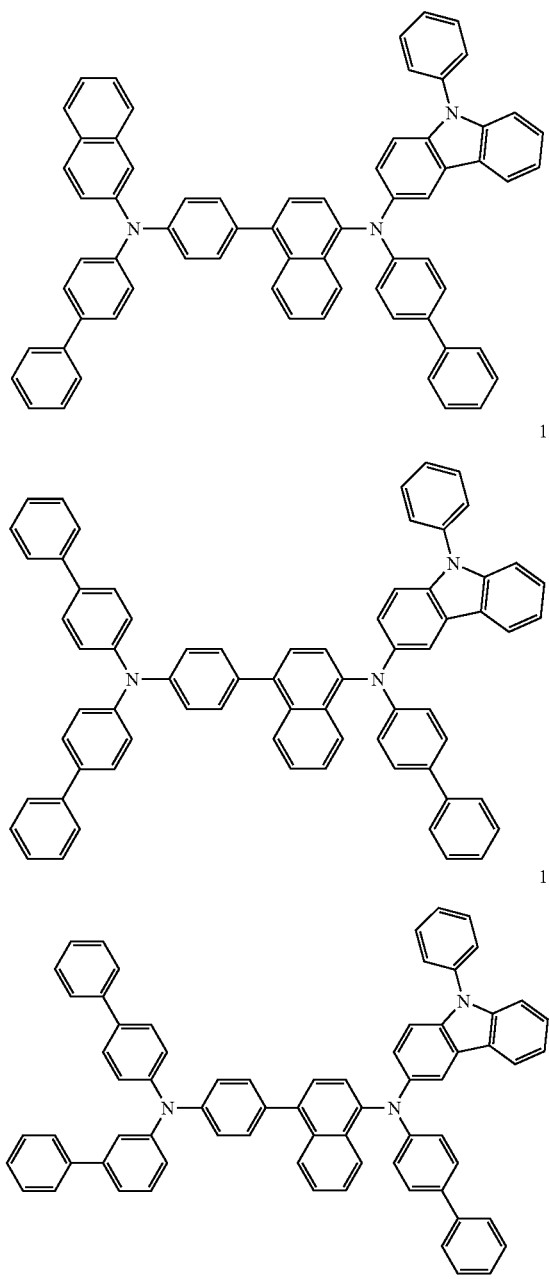

An OLED according to the present embodiments includes a first electrode, a second electrode, an organic layer interposed between the first electrode and the second electrode, wherein the organic layer includes a compound represented by Formula 1 or 2 described above. The organic layer including the compound of Formula 1 or 2 may be a HIL, a HTL, or a single layer having both hole injection and hole transport capabilities. Furthermore, the organic layer including the compound of Formula 1 or 2 may be an EML. In this regard, the compound of Formula 1 or 2 may be used as a host material for a blue, green, or red color producing fluorescent or phosphorescent material.

In some embodiments, the organic layer including the compound of Formula 1 or 2 is a HTL.

Meanwhile, the first electrode may be an anode, and the second electrode may be a cathode. Also, the first electrode may be a cathode, and the second electrode may be an anode.

The OLED may also include at least one layer selected from the group consisting of a HIL, a HTL, an electron blocking layer (EBL), an EML, a hole blocking layer (HBL), an electron transport layer (ETL) and an EIL. As desired, the organic layer may be a double layered organic layer.

For example, the OLED according to the present embodiments may have a first electrode/HIL/EML/second electrode structure, a first electrode/HIL/HTL/EML/ETL/second electrode structure, or a first electrode/HIL/HTL/EML/ETL/EIL/second electrode structure. The OLED may also have a first electrode/single layer having both hole injection and hole transport capabilities/EML/ETL/second electrode structure, or a first electrode/single layer having both hole injection and hole transport capabilities/EML/ETL/EIL/second electrode structure.

The OLED according to the present embodiments may be applied to a top emission type OLED, a bottom emission type OLED, or the like.

Hereinafter, a method of fabricating an OLED according to the present embodiments will be described with reference to FIG. 1. An OLED shown in FIG. 1 includes a substrate, a first electrode (anode), a HIL, a HTL, an EML, an ETL, an EIL, and a second electrode (cathode).

A first electrode is formed by depositing or sputtering a high work-function material on a substrate. The first electrode may be an anode or a cathode. The substrate, which can be any substrate that is used in conventional organic light emitting devices, may be a glass substrate or a transparent plastic substrate that has good mechanical strength, thermal stability, transparency, and surface smoothness, and is easily treatable, and waterproof The first electrode can comprise, for example, ITO, IZO, SnO$_2$, ZnO, Al, Ag, Mg, or the like, and formed as a transparent or reflective electrode.

A HIL may be formed on the first electrode by vacuum deposition, spin coating, casting, Langmuir Blodgett (LB), or the like.

When the HIL is formed by vacuum deposition, vacuum deposition conditions may vary according to the compound that is used to form the HIL, and the desired structure and thermal properties of the HIL to be formed. In some embodiments, vacuum deposition may be performed at a deposition temperature of from about 100° C. to about 500° C., under a pressure of from about $10^{-8}$ torr to about $10^{-3}$ torr, at a deposition speed of from about 0.01 to about 100 Å/sec, and to a layer thickness of from about 10 Å to about 5 μm.

When the HIL is formed by spin coating, coating conditions may vary according to a compound that is used to form the HIL, and the desired structure and thermal properties of the HIL to be formed. In some embodiments the coating speed may be in the range of about from about 2000 rpm to about 5000 rpm, and a temperature for heat treatment, which is performed to remove a solvent after coating, may be from about 80° C. to about 200° C.

The HIL can comprise the compound represented by Formula 1 or 2 described above. Alternatively, the material may be a phthalocyanine compound, such as copper phthalocyanine disclosed in U.S. Pat. No. 4,356,429; a star-burst type amine derivative, such as TCTA, m-MTDATA, and m-MTDAPB, disclosed in "Advanced Materials" magazine (USA), 6, p. 677 (1994); a soluble and conductive polymer such as polyaniline/Dodecylbenzenesulfonic acid (Pani/DBSA); poly(3,4-ethylenedioxythiophene)/Poly(4-styrenesulfonate (PEDOT/PSS): polyaniline/camphor sulfonic acid (Pani/CSA); (polyaniline)/poly(4-styrenesulfonate) (PANI/PSS); or the like.

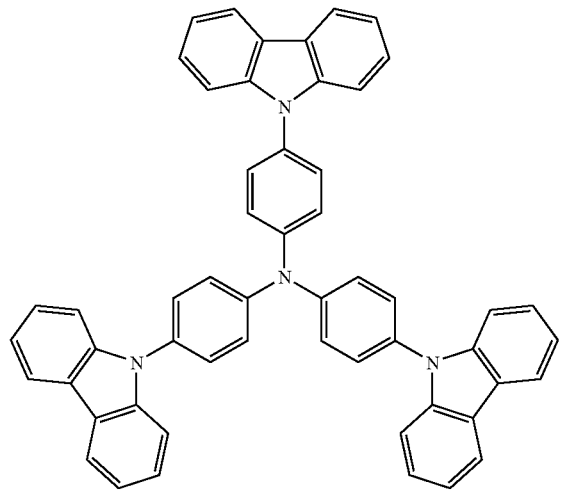

TCTA

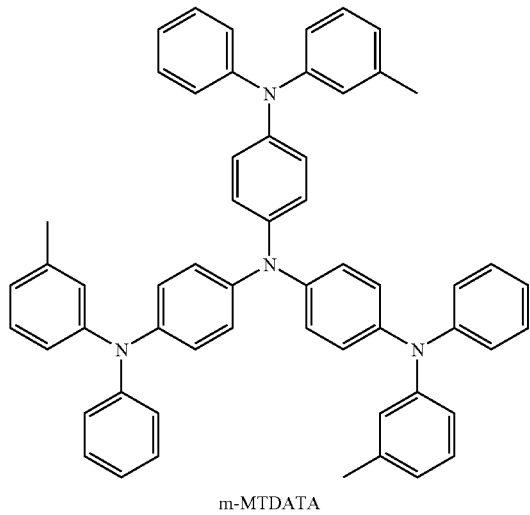

m-MTDATA

The thickness of the HIL may be from about 100 Å to about 10000 Å, and preferably, from about 100 Å to about 1000 Å.

A HTL can be formed on the HIL using a vacuum deposition method, a spin coating method, a casting method, LB, or the like. When the HTL is formed by vacuum deposition or spin coating, the conditions for deposition and coating are similar to those for the formation of the HIL, although conditions for the deposition and coating may vary according to the material that is used to form the HTL.

The HTL can comprise the compound represented by Formula 1 or 2 described above. The HTL may also be formed of any material that is conventionally used to form an HTL. For example, the HTL can be formed of a carbazole derivative, such as N-phenylcarbazole and polyvinylcarbazole; a typical amine derivative having an aromatic condensation ring such as 4,4'-bis[N-(1-naphthyl)-N-phenylamino]biphenyl (NPB), N,N'-bis(3-methylphenyl)-N,N'-diphenyl-[1,1-biphenyl]-4,4'-diamine (TPD), N,N'-di(naphthalene-1-yl)-N,N'-diphenyl benzydine (α-NPD); or the like.

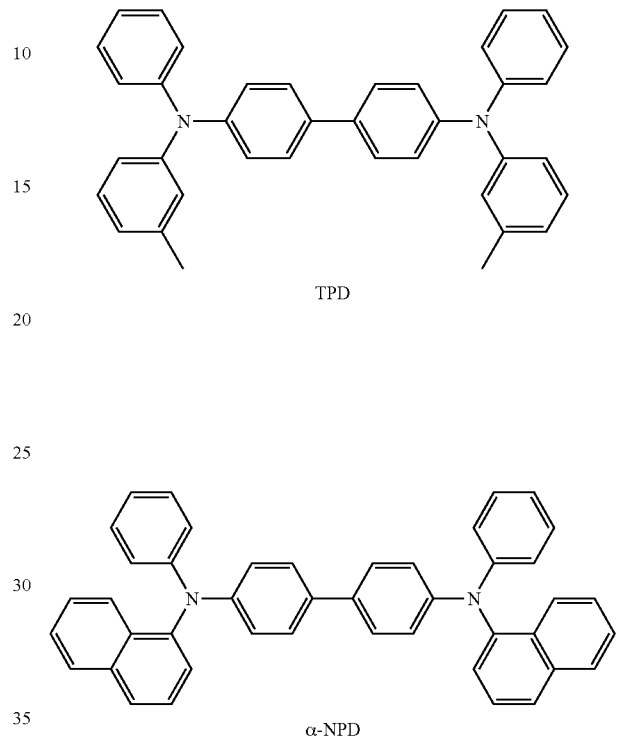

TPD

α-NPD

The thickness of the HTL may be from about 50 Å to about 1000 Å, and preferably, from about 100 Å to about 600 Å.

Then, an emissive layer (EML) can be formed on the HTL by vacuum deposition, spin coating, casting, LB, or the like. When the EML is formed by vacuum deposition or spin coating, the conditions for deposition and coating are similar to those for the formation of the HIL, although the conditions for deposition and coating may vary according to the material that is used to form the EML.

The EML may include the compound of Formula 1 or 2 described above. In particular, the compound of Formula 1 or 2 may be used as a host. The EML may be formed of a variety of emissive materials known in the art, and formed of a known host and dopant. Both of any fluorescent dopants and any phosphorescent dopants which are known in the art may be used as the dopant.

For example, the host material may be $Alq_3$, 4,4'-N,N'-dicarbazole-biphenyl (CBP), poly(N-vinylcarbazole) (PVK), distyrylarylene (DSA), and IDE215 (Idemitsu Co., Tokyo, Japan), but is not limited thereto.

Regarding the dopant material, a fluorescent dopant may be IDE102, IDE105, and IDE118 (Idemitsu Co.), and a phosphorescent dopant may be $Ir(ppy)_3$ (ppy=phenylpyridine) (green), $(4,6-F_2ppy)_2Irpic$ (Chihaya Adachi et al. *Appl. Phys. Lett.*, 79, 2082-2084, 2001), TEB002 (Covion GmbH (Frankfurt, Germany)), platinum(II) octaethylporphyrin (PtOEP), a compound represented by Formula 3 below (Korean Patent Publication No. 2005-0078472), Firpric, and a red phosphorescent dopant of RD 61 (UDC Co. Ltd.), but are not limited thereto.

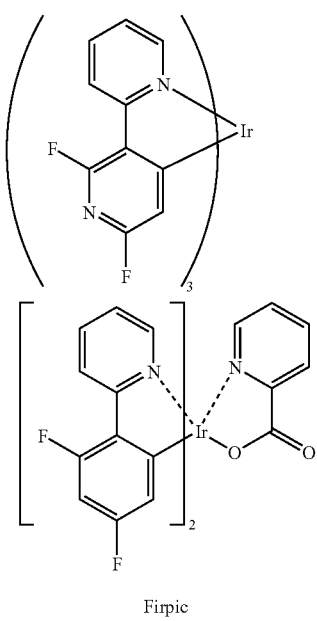

Formula 3

Firpic

The amount of the dopant may be from about 0.1 to about 20 parts by weight, and preferably from about 0.5 to about 12 parts by weight based on 100 parts by weight of a material that is used to form the EML (that is, the total weight of the host and the dopant).

The thickness of the EML may be from about 100 Å to about 1000 Å, and preferably, from about 200 Å to about 600 Å.

A HBL (shown in FIG. 1) may be formed on the EML in order to prevent diffusion of triplet excitons or holes into an ETL when the phosphorescent dopant is used to form the EML. The HBL may be formed of any material that is commonly used to form a HBL without limitation. Non-limiting examples of the material are an oxadiazole derivative, a triazole derivative, a phenanthroline derivative, a hole blocking material as disclosed in JP 11-329734(A1), Balq, and BCP.

The thickness of the HBL may be from about 50 Å to about 1000 Å, and preferably, from about 100 Å to about 300 Å.

An ETL is formed by vacuum deposition, spin coating, casting, or the like. When the ETL is formed by vacuum deposition or spin coating, the conditions for deposition and coating are, in general, similar to those for the formation of the HIL, although the conditions for the deposition and coating conditions may vary according to the material that is used to form the ETL.

The ETL may be formed of any material that is commonly used to form an ETL without limitation. The ETL may also include a quinoline derivative, in particular, tris(8-quinolinorate)aluminum ($Alq_3$), TAZ, or the like, which is known in the art.

The thickness of the ETL may be from about 100 Å to about 1000 Å, and preferably, from about 100 Å to about 500 Å.

Then, an EIL, which is formed of a material allowing easy injection of electrons from a cathode, can be formed on the ETL.

The EIL may be formed of LiF, NaCl, CsF, $Li_2O$, BaO, or the like, which is known in the art. Conditions for the deposition of the EIL are, in general, similar to conditions for the formation of the HIL, although they may vary according to the material that is used to form the EIL.

The thickness of the EIL may be from about 1 Å to about 100 Å, and preferably, from about 5 Å to about 90 Å.

A second electrode can be formed on the EIL by vacuum deposition, sputtering, or the like. The second electrode can be used as a cathode or an anode. The second electrode may comprise a low work-function metal, an alloy, an electrically conductive compound, or a combination of these. In some embodiments, the second electrode may comprise Li, Mg, Al, Al—Li, Ca, Mg—In, Mg—Ag, or the like. Alternatively, a transparent cathode formed of ITO or IZO can be used to produce a top emission light emitting device.

The OLED according to the present embodiments may be applied to a variety of flat panel display devices such as a passive matrix organic light emitting display device and an active matrix organic light emitting display device. In particular, if the OLED is applied to an active matrix organic light emitting display device, a first electrode in a substrate which is a pixel electrode may be electrically connected to a source electrode or a drain electrode of a thin film transistor. In addition, the OLED may also be applied to a flat panel display device having a both-side emission structure.

Hereinafter, synthesis examples of Compounds 8, 71, 8, and 89 and examples will be described in detail. However, the synthesis examples and examples are provided to facilitate the understanding of the present embodiments only, and are not intended to limit the scope of the present embodiments.

EXAMPLES

Synthesis Example 1

Synthesis of Compound 1

Compound 1 was synthesized through Reaction Scheme 1 below.

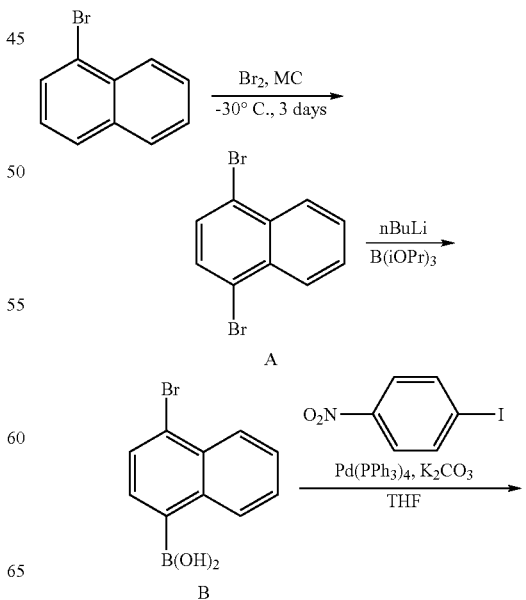

Reaction Scheme 1

-continued

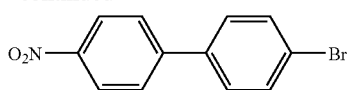

C

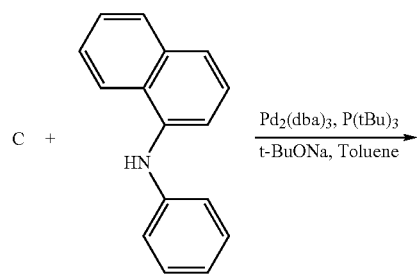

C + [amine]  →(Pd₂(dba)₃, P(tBu)₃ / t-BuONa, Toluene)

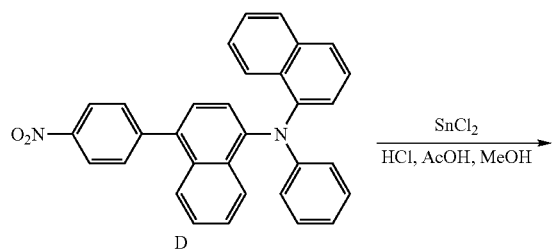

D →(SnCl₂ / HCl, AcOH, MeOH)

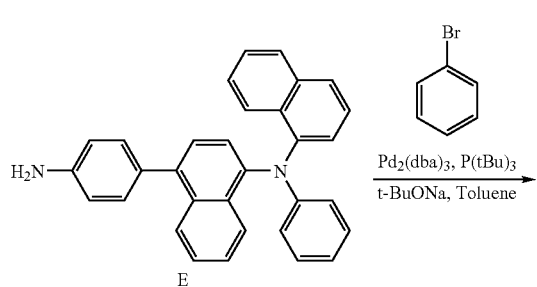

E + PhBr →(Pd₂(dba)₃, P(tBu)₃ / t-BuONa, Toluene)

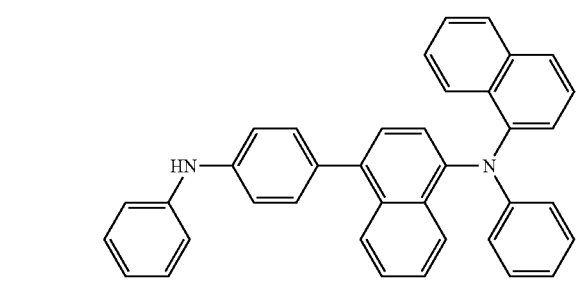

F

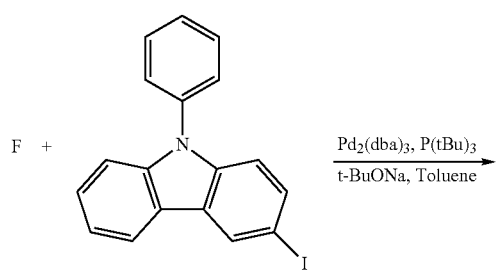

F + [carbazole-I] →(Pd₂(dba)₃, P(tBu)₃ / t-BuONa, Toluene)

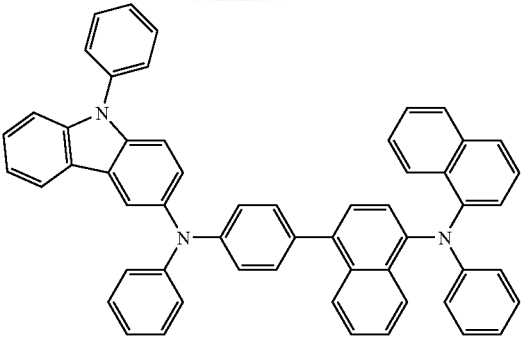

1

Synthesis of Intermediate A 20.7 g (100 mmol) of 1-bromonaphthalene was dissolved in 300 mL of dichloromethane, and the temperature was set to −30°. A solution including 2.56 g (50 mmol) of bromine dissolved in 30 mL of dichloromethane at −30° was gradually added thereto. The mixture was put in a light-tight environment and placed in a freezer at −30° for 48 hours. After the reaction was completed, the mixture was subjected to extraction by adding a 10% sodium thiosulfate solution to the mixture. An organic layer was collected and dried using magnesium sulfate to evaporate the solvent. The residue was recrystallized using diethyl ether and n-hexane to obtain 24.3 g of a white solid Intermediate A (Yield: 85%).

$^1$H NMR (CDCl$_3$, 400 MHz) δ (ppm)—8.26-8.24 (m, 2H), 7.66-7.63 (m, 4H)

$^{13}$C NMR (CDCl$_3$, 100 MHz) δ (ppm)—132.9, 130.0, 128.2, 127.8, 122.6.

Synthesis of Intermediate B 14.3 g (50 mmol) of Intermediate A was dissolved in 150 mL of diethyl ether, and 20 mL of n-butyl lithium (2.5 M in Hexane) was added thereto at −78°. After 30 minutes, the temperature was gradually increased up to room temperature. After 30 minutes, the mixture was added to 23 mL (100 mmol) of triisopropyl borate dissolved in 50 mL of diethyl ether at −78°. The mixture was stirred at room temperature for 5 hours, and water was added thereto. The mixture was washed three times with 200 mL of diethyl ether. The washed diethyl ether layer was dried using MgSO$_4$ and further dried under a reduced pressure. The resultant was recrystallized in n-hexane to obtain 9.6 g of a white solid Intermediate B (Yield: 77%).

$^1$H NMR (CDCl$_3$, 400 MHz) δ (ppm)—8.05 (d, 1H), 7.85 (d, 1H), 7.73 (m, 4H), 7.35 (s, 2H)

$^{13}$C NMR (CDCl$_3$, 100 MHz) δ (ppm)—141.4, 131.0, 130.8, 130.4, 130.1, 127.0, 126.2, 102.2, 101.0.

Synthesis of Intermediate C 7.53 g (30 mmol) of Intermediate B, 15 g (60 mmol) of 4-iodobenzene nitride, 1.7 g (1.5 mmol) of Pd(PPh$_3$)$_4$, and 20 g (150 mmol) of K$_2$CO$_3$ were dissolved in 100 mL of a THF/H$_2$O (2:1) solution, and the mixture was stirred at 80° for 5 hours. The mixture was subjected to extraction three times with 200 mL of diethyl ether. An organic layer was collected and dried using magnesium sulfate to evaporate the solvent. The residue was recrystallized using dichloromethane and n-hexane to obtain 7.68 g of Intermediate C (Yield: 78%).

$^1$H NMR (CDCl$_3$, 400 MHz) δ (ppm)—8.14 (d, 1H), 8.10-8.06 (m, 2H), 7.86 (d, 1H), 7.81-7.71 (m, 2H), 7.66 (d, 1H), 7.58-7.53 (m, 3H)

$^{13}$C NMR (CDCl3, 100 MHz) δ (ppm)—149.8, 147.6, 137.1, 134.0, 131.4, 130.4, 129.8, 129.6, 128.6, 127.0, 123.9, 123.5, 123.3.

Synthesis of Intermediate D 5 g (15.2 mmol) of Intermediate C, 4 g (18.2 mmol) of 1-naphthylphenyl amine, 2.2 g (23 mmol) of t-BuONa, 0.95 g (0.3 mmol) of Pd$_2$(dba)$_3$, and 0.061 g (0.3 mmol) of P(t-Bu)$_3$ were dissolved in 500 mL of toluene, and the mixture was stirred at 90° for 3 hours. After the reaction was completed, the mixture was cooled to room temperature and subjected to extraction three times using distilled water and 50 mL of diethyl ether. An organic layer was collected and dried using magnesium sulfate to evaporate the solvent. The residue was separately purified by silica gel column chromatography to obtain 4.6 g of Intermediate D (Yield: 65%).

$^1$H NMR (CDCl$_3$, 400 MHz) δ (ppm)—8.49 (dd, 1H), 8.10-8.06 (dd, 3H), 7.85 (dd, 1H), 7.67-7.27 (m, 13H), 6.64-6.60 (m, 1H), 6.10 (d, 1H), 5.65 (dd, 2H)

$^{13}$C NMR (CDCl3, 100 MHz) δ (ppm)—156.1, 153.3, 153.2, 149.8, 143.1, 134.5, 134.0, 133.4, 133.2, 132.7, 132.3, 129.5, 128.5, 128.1, 126.5, 126.0, 125.9, 125.8, 125.5, 125.0, 124.1, 123.9, 123.6, 121.7, 121.5, 117.3, 116.6.

Synthesis of Intermediate E 4.6 g (10 mmol) of Intermediate D was dissolved in 20 mL of acetic acid and 10 mL of methyl alcohol. 189 mg (1 mmol) of SnCl$_2$ and a small amount of HCl were added thereto, and the mixture was stirred at 80° for 5 hours. After the reaction was completed, the mixture was cooled to room temperature and subjected to extraction three times using distilled water and 50 mL of diethyl ether. An organic layer was collected and dried using magnesium sulfate to evaporate the solvent. The residue was separately purified using silica gel column chromatography to obtain 3.88 g of Intermediate E (Yield: 89%).

$^1$H NMR (CDCl$_3$, 400 MHz) δ (ppm)—8.49 (dd, 1H), 8.04 (d, 1H), 7.85 (dd, 1H), 7.65-7.27 (m, 13H), 6.70-6.60 (m, 3H), 6.10 (dd, 1H), 5.65 (dd, 2H), 5.48 (s, 2H), $^{13}$C NMR (CDCl3, 100 MHz) δ (ppm)—156.1, 135.3, 153.2, 147.7, 135.4, 134.5, 133.4, 133.3, 133.2, 132.3, 132.0, 129.5, 128.5, 128.1, 127.5, 126.0, 125.9, 125.5, 125.0, 124.1, 123.7, 123.6, 121.7, 121.5, 117.3, 116.6, 115.6.

Synthesis of Intermediate F 4.4 g (10 mmol) of Intermediate E, 1.05 mL (10 mmol) of bromobenzene, 1.4 g (15 mmol) of t-BuONa, 0.18 g (0.2 mmol) of Pd$_2$(dba)$_3$, and 0.04 g (0.2 mmol) of P(t-Bu)$_3$ were dissolved in 40 mL of toluene, and the mixture was stirred at 90° for 3 hours. After the reaction was completed, the mixture was cooled to room temperature, and subjected to extraction three times using distilled water and 40 mL of diethyl ether. An organic layer was collected and dried using magnesium sulfate to evaporate the solvent. The residue was separately purified using silica gel column chromatography to obtain 3.07 g of Intermediate F (Yield: 60%).

$^1$H NMR (CDCl$_3$, 400 MHz) δ (ppm)—8.49 (dd, 1H), 8.05 (d, 1H), 7.85 (dd, 1H), 7.63-7.25 (m, 15H), 7.12 (d, 2H), 6.90-6.60 (m, 4H), 6.10 (dd, 1H), 5.65 (d, 2H), 5.51 (s, NH)

$^{13}$C NMR (CDCl3, 100 MHz) δ (ppm)—156.1, 153.3, 153.2, 143.2, 142.3, 134.5, 133.4, 133.2, 132.8, 132.5, 132.3, 131.1, 129.5, 129.4, 129.0, 128.5, 128.1, 126.0, 125.9, 125.5, 125.0, 124.1, 123.7, 123.6, 121.7, 121.5, 119.1, 117.4, 117.3, 116.6, 116.5.

Synthesis of Compound 1

5.1 g (10 mmol) of Intermediate F, 4.06 g (11 mmol) of 9-phenyl-3-iodocarbazole, 1.4 g (15 mmol) of t-BuONa, 0.18 g (0.2 mmol) of Pd$_2$(dba)$_3$, and 0.04 g (0.2 mmol) of P(t-Bu)$_3$ were dissolved in 40 mL of toluene, and the mixture was stirred at 90° for 3 hours. After the reaction was completed, the mixture was cooled to room temperature, and subjected to extraction three times using distilled water and 40 mL of diethyl ether. An organic layer was collected and dried using magnesium sulfate to evaporate the solvent. The residue was separately purified using silica gel column chromatography to obtain 6.78 g of Compound 1 (Yield: 90%).

$^1$H NMR (CDCl$_3$, 400 MHz) δ (ppm)—8.49 (dd, 1H), 8.20 (d, 1H), 7.94-7.84 (m, 2H), 7.65-7.27 (m, 26H), 6.64-6.60 (m, 2H), 6.43-6.40 (m, 2H), 6.10 (d, 1H), 5.69-5.64 (m, 4H)

$^{13}$C NMR (CDCl$_3$, 100 MHz) δ (ppm)—156.1, 153.3, 153.2, 151.4, 148.3, 142.5, 137.9, 137.7, 136.4, 134.8, 134.5, 133.9, 133.4, 133.2, 132.3, 129.8, 129.5, 129.4, 129.2, 128.5, 128.1, 127.9, 127.4, 127.1, 126.3, 126.0, 125.9, 125.5, 125.1, 125.0, 124.1, 123.6, 123.4, 122.9, 121.7, 121.5, 120.4, 118.1, 117.3, 117.0, 116.7, 116.6, 114.4, 111.5, 108.4.

Synthesis Example 2

Synthesis of Compound 8

Compound 8 was synthesized through Reaction Scheme 2 below.

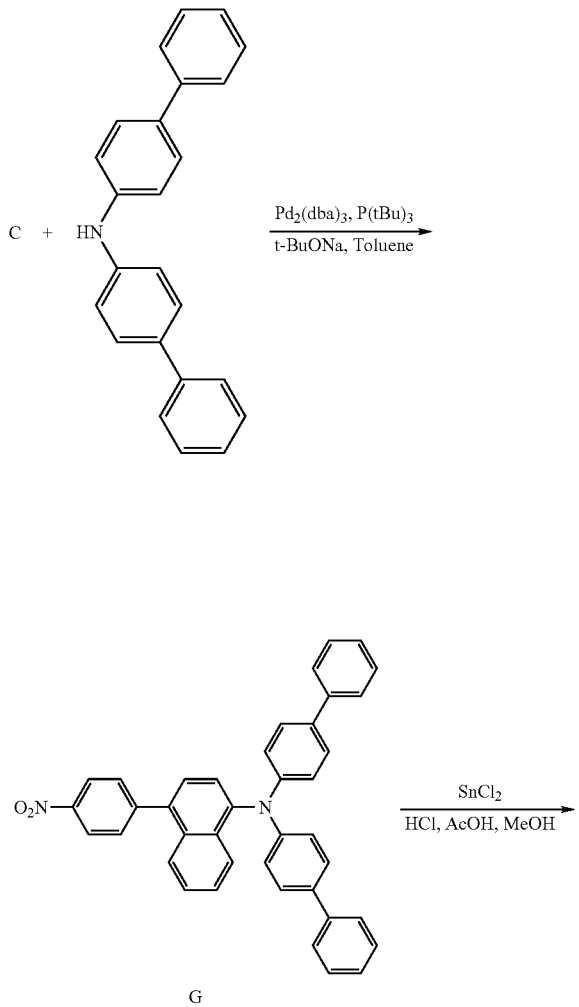

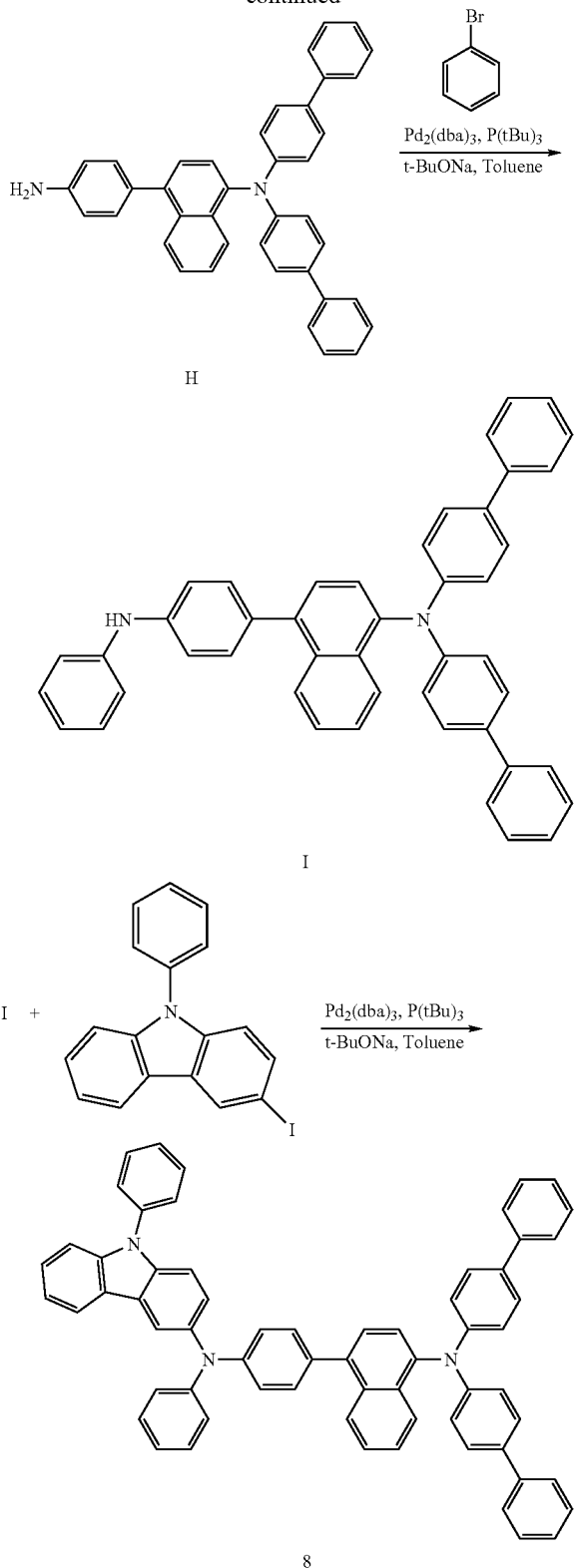

Synthesis of Intermediate G 3.28 g (10 mmol) of Intermediate C, 3.54 g (11 mmol) of N,N-biphenyl amine, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature, and subjected to extraction three times using distilled water and 40 mL of diethyl ether. An organic layer was collected and dried using magnesium sulfate to evaporate the solvent. The residue was separately purified using silica gel column chromatography to obtain 4.83 g of Intermediate G (Yield: 85%).

$^1$H NMR (CDCl$_3$, 400 MHz) δ (ppm)—8.10-8.06 (m, 3H), 7.76-7.74 (m, 4H), 7.66-7.61 (m, 8H), 7.54 (d, 1H), 7.41-7.29 (m, 8H), 6.45-6.41 (m, 4H)

$^{13}$C NMR (CDCl3, 100 MHz) δ (ppm)—151.2, 150.9, 149.8, 143.1, 136.9, 136.1, 135.4, 134.0, 132.9, 132.7, 128.9, 128.8, 128.1, 127.2, 125.9, 124.7, 124.1, 123.9, 123.6, 122.1, 117.9, 117.1.

Synthesis of Intermediate H 5.68 g (10 mmol) of Intermediate G was dissolved in 20 mL of acetic acid and 10 mL of methyl alcohol. 189 mg (1 mmol) of SnCl$_2$ and a small amount of HCl were added thereto, and the mixture was stirred at 80° for 5 hours. After the reaction was completed, the mixture was cooled to room temperature and subjected to extraction 5 times using distilled water and 50 mL of diethyl ether. An organic layer was collected and dried using magnesium sulfate to evaporate the solvent. The residue was separately purified using silica gel column chromatography to obtain 4.9 g of Intermediate E (Yield: 91%).

$^1$H NMR (CDCl$_3$, 400 MHz) δ (ppm)—8.04 (d, 1H), 7.75-7.73 (m, 4H), 7.66-7.61 (m, 6H), 7.55 (d, 1H), 7.39-7.29 (m, 10H), 6.70-6.66 (m, 2H), 6.45-6.41 (m, 4H), 5.48 (s, NH$_2$)

$^{13}$C NMR (CDCl3, 100 MHz) δ (ppm)—151.2, 150.9, 147.7, 136.9, 136.1, 135.4, 133.3, 132.9, 132.0, 128.9, 128.8, 128.1, 127.2, 125.9, 125.7, 124.1, 123.6, 119.9, 117.9, 117.1, 115.6.

Synthesis of Intermediate I 5.4 g (10 mmol) of Intermediate H, 1.05 mL (11 mmol) of bromobenzene, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 3.87 g of Intermediate I (Yield: 63%).

$^1$H NMR (CDCl$_3$, 400 MHz) δ (ppm)—8.05 (d, 1H), 7.75 (d, 4H), 7.66-7.61 (m, 6H), 7.54-7.49 (m, 3H), 7.39-7.25 (m, 10H), 7.12 (d, 2H), 6.90-6.87 (m, 1H), 6.78-6.75 (m, 2H), 6.45-6.41 (m, 4H), 5.51 (s, NH)

$^{13}$C NMR (CDCl3, 100 MHz) δ (ppm)—151.2, 150.9, 143.2, 142.3, 136.9, 136.1, 135.4, 132.9, 132.8, 132.5, 131.1, 129.4, 128.9, 128.8, 128.1, 127.2, 127.1, 125.9, 124.1, 123.6, 119.9, 119.1, 117.9, 117.4, 117.1, 116.5.

Synthesis of Compound 8

6.14 g (10 mmol) of Intermediate I, 4.06 g (11 mmol) of 9-phenyl-3-iodocarbazole, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 7.96 g of Compound 8 (Yield: 93%).

$^1$H NMR (CDCl$_3$, 400 MHz) δ (ppm)—8.21 (d, 1H), 7.93 (d, 1H), 7.74 (dd, 4H), 7.66-7.29 (m, 30H), 6.64-6.61 (m, 1H), 6.44-6.40 (m, 6H), 5.69 (dd, 2H)

$^{13}$C NMR (CDCl3, 100 MHz) δ (ppm)—151.4, 151.2, 150.9, 148.3, 142.5, 137.9, 137.7, 136.9, 136.4, 136.1, 135.4, 134.8, 133.9, 132.9, 129.8, 129.4, 129.2, 128.9, 128.8, 128.1, 127.4, 127.2, 127.1, 126.3, 126.1, 125.9, 124.1, 123.6, 123.4, 122.9, 121.3, 120.4, 118.1, 117.9, 117.3, 117.1, 117.0, 116.7, 114.4, 111.5, 108.4.
Synthesis Example 3
Synthesis of Compound 64
Compound 64 was synthesized through Reaction Scheme 3 below.
Reaction Scheme 3
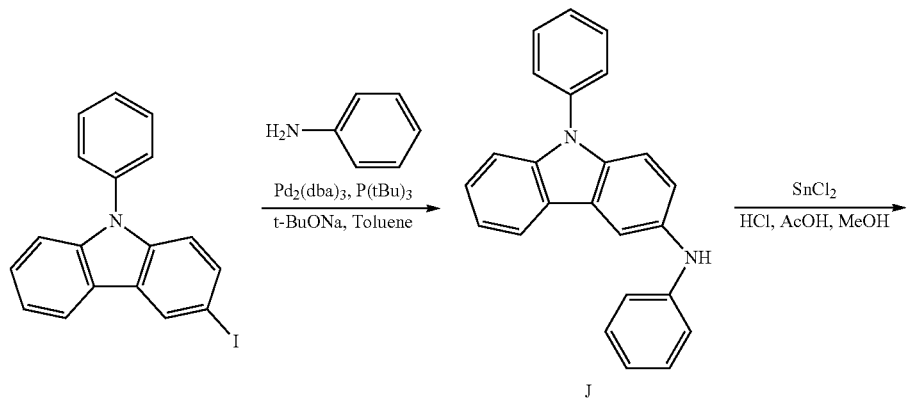
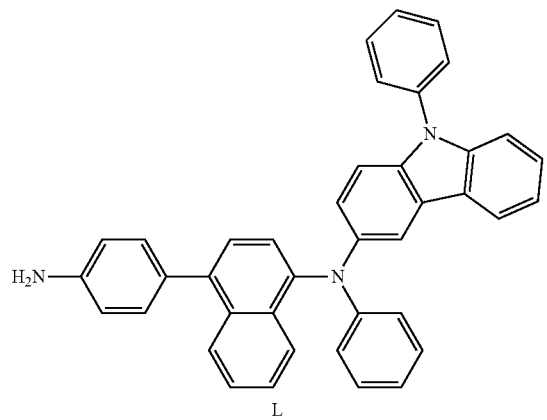
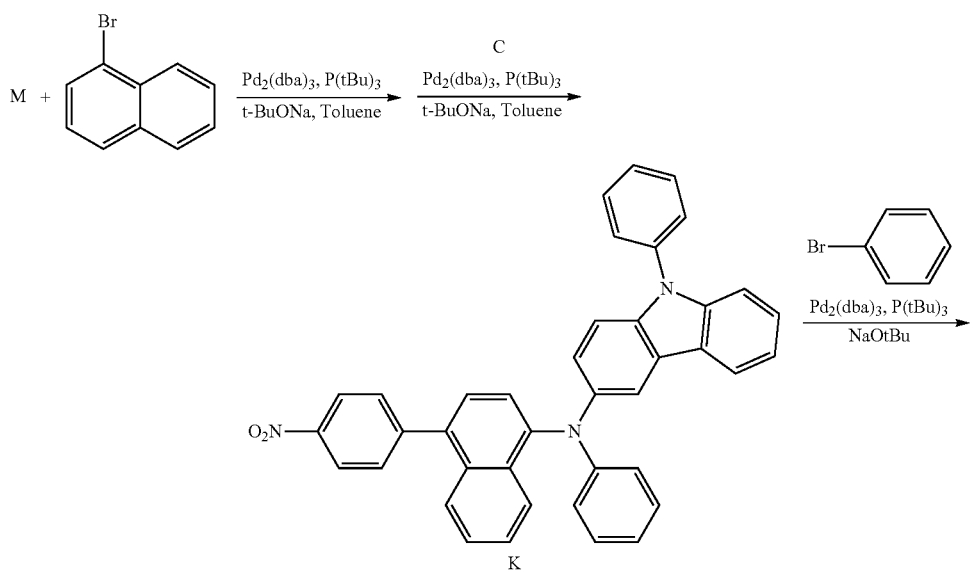

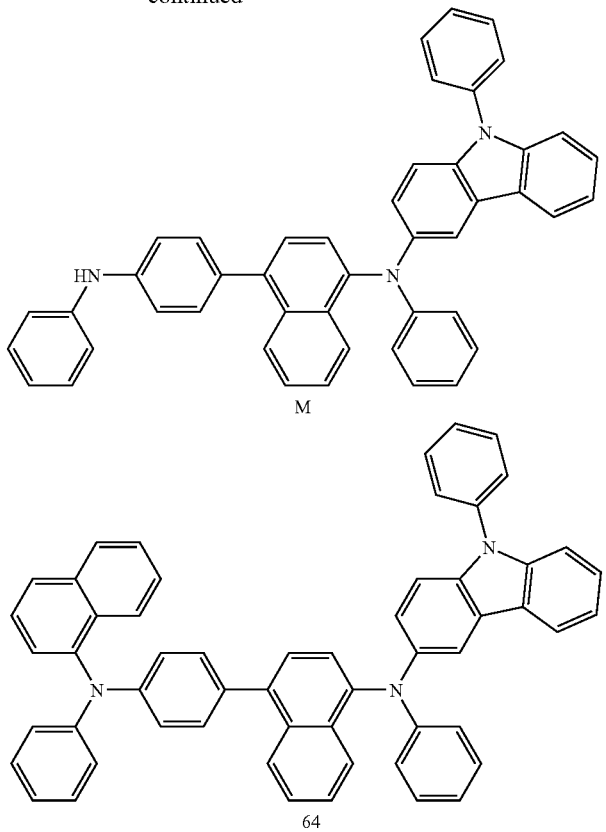

Synthesis of Intermediate J 3.69 g (10 mmol) of 9-phenyl-3-iodocarbazole, 1.4 g (15 mmol) of aniline, 1.4 g (15 mmol) oft-BuONa, 0.18 g (0.2 mmol) of Pd$_2$(dba)$_3$, and 0.04 g (0.2 mmol) of P(t-Bu)$_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 3.04 g of Intermediate J (Yield: 91%).

$^1$H NMR (CDCl$_3$, 400 MHz) δ (ppm)—8.03-7.99 (m, 1H), 7.67 (d, 1H), 7.49 (d, 4H), 7.43 (d, 1H), 7.34-7.33 (m, 4H), 7.20-7.16 (m, 2H), 7.02 (dd, 2H), 6.95 (dd, 1H), 6.75-6.71 (m, 1H), 5.68 (s, NH)

$^{13}$C NMR (CDCl3, 100 MHz) δ (ppm)—144.7, 139.9, 137.4, 135.7, 129.8, 129.4, 128.1, 127.4, 127.1, 126.3, 119.1, 118.7, 118.5, 116.8, 113.1, 111.2, 109.4, 102.5.

Synthesis of Intermediate K 3.28 g (10 mmol) of Intermediate C, 3.7 g (11 mmol) of Intermediate J, 1.4 g (15 mmol) of t-BuONa, 0.18 g (0.2 mmol) of Pd$_2$(dba)$_3$, and 0.04 g (0.2 mmol) of P(t-Bu)$_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 4.77 g of Intermediate K (Yield: 82%).

$^1$H NMR (CDCl$_3$, 400 MHz) δ (ppm)—8.10-8.07 (m, 3H), 7.93 (d, 1H), 7.68-7.61 (m, 4H), 7.55-7.28 (m, 16H), 6.64-6.60 (m, 1H), 5.66 (dd, 2H)

$^{13}$C NMR (CDCl3, 100 MHz) δ (ppm)—153.3, 150.6, 149.8, 146.1, 143.1, 137.9, 137.7, 136.4, 134.0, 132.7, 131.6, 131.4, 129.8, 128.1, 127.4, 127.1, 126.3, 125.9, 124.7, 124.1, 123.9, 123.6, 122.3, 122.1, 120.4, 118.1, 117.2, 116.7, 116.4, 116.2, 111.7, 108.4.

Synthesis of Intermediate L 5.82 g (10 mmol) of Intermediate K was dissolved in 20 mL of acetic acid and 10 ml of methyl alcohol. 189 mg (1 mmol) of SnCl$_2$ and a small amount of HCl were added thereto, and the mixture was stirred at 80° for 5 hours. After the reaction was completed, the mixture was cooled to room temperature and subjected to extraction 5 times using distilled water and 50 mL of diethyl ether. An organic layer was collected and dried using magnesium sulfate to evaporate the solvent. The residue was separately purified using silica gel column chromatography to obtain 4.9 g of Intermediate L (Yield: 89%).

$^1$H NMR (CDCl$_3$, 400 MHz) δ (ppm)—8.04 (d, 1H), 7.93 (d, 1H), 7.65-7.60 (m, 2H), 7.54-7.28 (m, 18H), 6.70-6.60 (m, 3H), 5.66 (d, 2H), 5.48 (s, NH$_2$)

$^{13}$C NMR (CDCl3, 100 MHz) δ (ppm)—153.3, 150.6, 147.7, 146.1, 137.9, 137.7, 136.4, 135.4, 133.3, 132.0, 131.6, 131.4, 129.8, 128.1, 127.4, 127.1, 126.3, 125.9, 125.7, 124.1, 123.6, 122.3, 120.4, 119.9, 118.1, 117.2, 116.7, 116.4, 116.2, 115.6, 111.7, 108.4.

Synthesis of Intermediate M 5.51 g (10 mmol) of Intermediate L, 1.05 mL (11 mmol) of bromobenzene, 1.4 g (15 mmol) of t-BuONa, 0.18 g (0.2 mmol) of Pd$_2$(dba)$_3$, and 0.04 g (0.2 mmol) of P(t-Bu)$_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 4.2 g of Intermediate M (Yield: 67%).

$^1$H NMR (CDCl$_3$, 400 MHz) δ (ppm)—8.05 (d, 1H), 7.93 (d, 1H), 7.65-7.11 (m, 24H), 6.90-6.86 (m, 1H), 6.78-6.76 (m, 2H), 6.64-6.60 (m, 1H), 5.66 (dd, 2H), 5.51 (s, NH)

$^{13}$C NMR (CDCl$_3$, 100 MHz) δ (ppm)—153.3, 150.6, 146.1, 143.2, 142.3, 137.9, 137.7, 136.4, 132.8, 132.5, 131.6, 131.4, 131.1, 129.8, 129.4, 128.1, 127.4, 127.1, 126.3, 125.9, 124.1, 123.6, 122.3, 120.4, 119.9, 119.1, 118.1, 117.4, 117.2, 116.7, 116.5, 116.4, 116.2, 111.7, 108.4.

Synthesis of Compound 64

6.27 g (10 mmol) of Intermediate M, 2.3 g (11 mmol) of 1-bromonaphthalene, 1.4 g (15 mmol) of t-BuONa, 0.18 g separately purified using silica gel column chromatography to obtain 6.48 g of Intermediate K (Yield: 86%).

$^1$H NMR (CDCl$_3$, 400 MHz) δ (ppm)—8.50 (dd, 1H), 8.21 (d, 1H), 7.93 (d, 1H), 7.85 (d, 1H), 7.65-7.59 (m, 3H), 7.54-7.28 (m, 23H), 6.64-6.60 (m, 2H), 6.41-6.38 (m, 2H), 6.13 (d, 1H), 5.67 (dd, 4H)

$^{13}$C NMR (CDCl$_3$, 100 MHz) δ (ppm)—154.0, 153.3, 150.6, 149.7, 149.6, 146.1, 137.9, 137.7, 136.4, 135.8, 134.8, 131.6, 131.5, 131.4, 129.8, 129.2, 128.6, 128.1, 127.6, 127.4, 127.1, 126.7, 126.3, 126.1, 126.0, 125.9, 124.8, 124.1, 123.6, 122.3, 121.7, 121.5, 121.3, 120.4, 118.1, 117.2, 116.7, 116.4, 116.2, 111.7, 108.4.

Synthesis Example 4

Synthesis of Compound 71

Compound 71 was synthesized through Reaction Scheme 4 below.

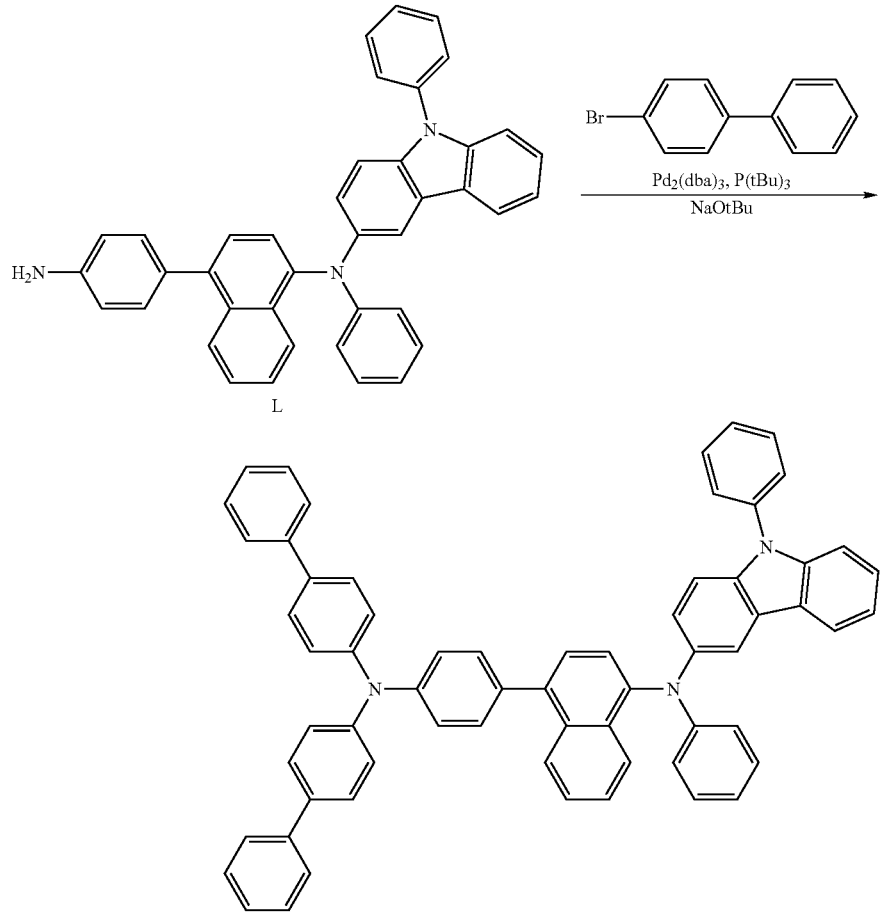

(0.2 mmol) of Pd$_2$(dba)$_3$, and 0.04 g (0.2 mmol) of P(t-Bu)$_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was Synthesis of Compound 71

5.51 g (10 mmol) of Intermediate L, 5.12 g (22 mmol) of bromobiphenyl, 2.8 g (30 mmol) of t-BuONa, 0.36 g (0.4 mmol) of Pd$_2$(dba)$_3$, and 0.08 g (0.4 mmol) of P(t-Bu)$_3$ were dissolved in 50 mL of toluene, and the mixture was stirred at 90° for 3 hours. After the reaction was completed, the mixture was cooled to room temperature and subjected to extraction 5 times using distilled water and 50 mL of diethyl ether. An organic layer was collected and dried using magnesium sulfate to evaporate the solvent. The residue was separately purified using silica gel column chromatography to obtain 6.42 g of Compound 71 (Yield: 75%).

$^1$H NMR (CDCl$_3$, 400 MHz) δ (ppm)—8.21 (d, 1H), 7.93 (d, 1H), 7.75 (dd, 3H), 7.68-7.60 (m, 6H), 7.55-7.28 (m, 25H), 6.64-6.61 (m, 1H), 6.46-6.41 (m, 6H), 5.66 (dd, 2H)

$^{13}$C NMR (CDCl$_3$, 100 MHz) δ (ppm)—153.3, 150.6, 149.3, 147.4, 146.1, 137.9, 137.7, 136.9, 136.4, 135.4, 134.8, 134.2, 133.9, 131.6, 131.4, 129.8, 129.2, 128.9, 128.8, 128.1, 127.4, 127.2, 127.1, 126.3, 126.1, 125.9, 124.1, 123.6, 122.3, 121.3, 120.4, 118.1, 117.9, 117.7, 117.2, 116.7, 116.4, 116.2, 111.7, 108.4.

Synthesis Example 5

Synthesis of Compound 80

Compound 80 was synthesized through Reaction Scheme 5 below.

Reaction Scheme 5

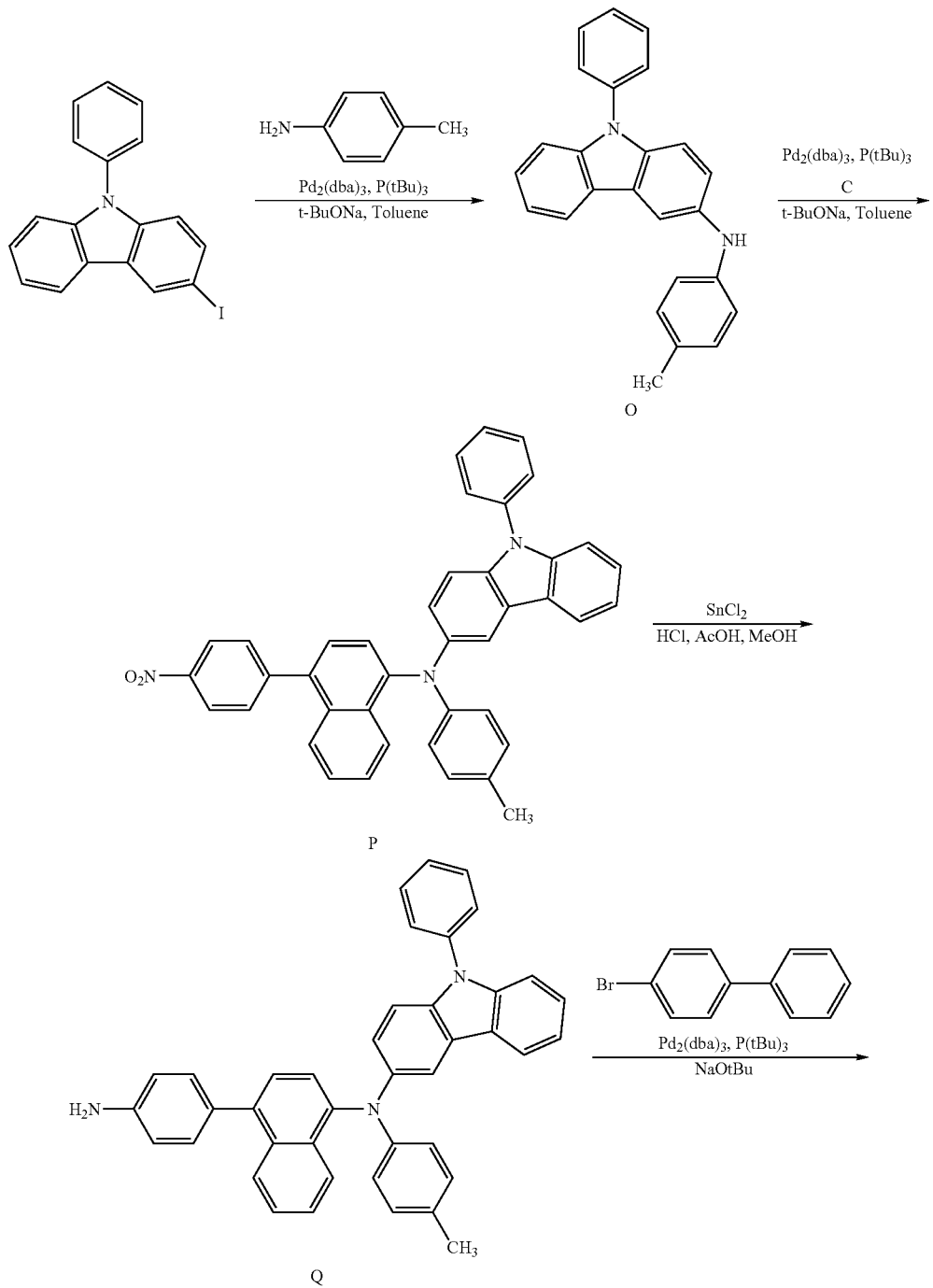

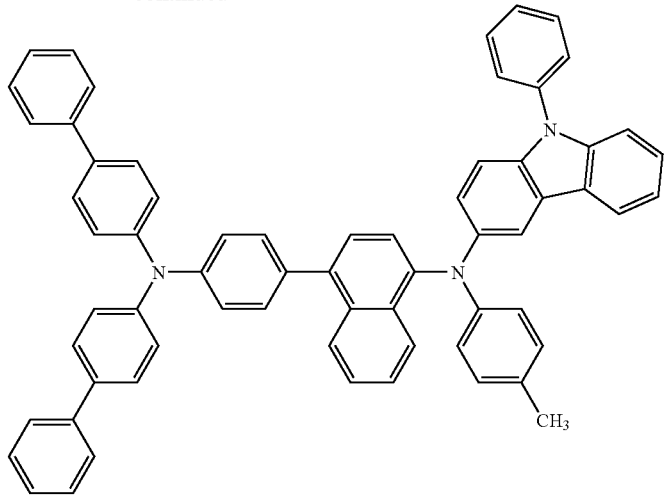

80

Synthesis of Intermediate O 3.69 g (10 mmol) of 9-phenyl-3-iodocarbazole, 1.6 g (15 mmol) of p-toluidine, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 3.27 g of Intermediate O (Yield: 94%).

$^1$H NMR ($CDCl_3$, 400 MHz) δ (ppm)—8.02 (t, 1H), 7.67 (s, 1H), 7.50-7.33 (m, 9H), 7.05-6.86 (m, 5H), 5.68 (s, NH), 2.25 (s, 3H)

$^{13}$C NMR (CDCl3, 100 MHz) δ (ppm)—140.2, 139.9, 137.4, 135.7, 129.8, 129.7, 128.1, 127.4, 127.1, 126.3, 119.1, 118.7, 118.5, 113.1, 111.2, 109.4, 102.5, 20.4.

Synthesis of Intermediate P 3.28 g (10 mmol) of Intermediate C, 3.83 g (11 mmol) of Intermediate O, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 4.59 g of Intermediate P (Yield: 77%).

$^1$H NMR ($CDCl_3$, 400 MHz) δ (ppm)—8.09-8.07 (m, 3H), 7.94 (d, 1H), 7.67-7.61 (m, 4H), 7.54-7.34 (m, 14H), 7.05 (d, 2H), 6.24 (d, 2H), 2.27 (s, 3H)

$^{13}$C NMR (CDCl3, 100 MHz) δ (ppm)—153.3, 151.3, 149.8, 146.1, 143.1, 137.9, 137.7, 136.4, 134.6, 134.0, 132.7, 131.4, 129.8, 129.7, 128.1, 127.4, 127.1, 126.3, 125.9, 124.7, 124.1, 123.9, 123.6, 122.3, 122.1, 121.2, 120.4, 118.1, 117.2, 116.7, 116.4, 116.2, 111.7, 108.4, 20.4.

Synthesis of Intermediate Q 5.95 g (10 mmol) of Intermediate P was dissolved in 20 mL of acetic acid and 10 mL of methyl alcohol. 189 mg (1 mmol) of $SnCl_2$ and a small amount of HCl were added thereto, and the mixture was stirred at 80° for 5 hours. After the reaction was completed, the mixture was cooled to room temperature and subjected to extraction 5 times using distilled water and 50 mL of diethyl ether. An organic layer was collected and dried using magnesium sulfate to evaporate the solvent. The residue was separately purified using silica gel column chromatography to obtain 4.92 g of Intermediate Q (Yield: 87%).

$^1$H NMR ($CDCl_3$, 400 MHz) δ (ppm)—8.04 (d, 1H), 7.94 (d, 1H), 7.65-7.34 (m, 18H), 7.05 (d, 2H), 6.70-6.66 (m, 2H), 6.24 (d, 2H), 5.48 (s, NH2), 2.27 (s, 3H)

$^{13}$C NMR (CDCl3, 100 MHz) δ (ppm)—153.3, 151.3, 147.7, 146.1, 137.9, 137.7, 136.4, 135.4, 134.6, 133.3, 132.0, 131.4, 129.8, 129.7, 128.1, 127.4, 127.1, 126.3, 125.9, 125.7, 124.1, 123.6, 122.3, 121.2, 120.4, 119.9, 118.1, 117.2, 116.7, 116.4, 116.2, 115.6, 111.7, 108.4, 20.4.

Synthesis of Compound 80

5.65 g (10 mmol) of Intermediate Q, 2.56 g (11 mmol) of bromobiphenyl, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 7.13 g of Compound 80 (Yield: 82%).

$^1$H NMR ($CDCl_3$, 400 MHz) δ (ppm)—8.21 (d, 1H), 7.94 (d, 1H), 7.75-7.31 (m, 32H), 7.05 (d, 2H), 6.47-6.41 (m, 6H), 6.24 (d, 2H), 2.27 (s, 3H)

$^{13}$C NMR (CDCl3, 100 MHz) δ (ppm)—153.3, 151.3, 149.3, 147.4, 146.1, 137.9, 137.7, 136.9, 136.4, 135.4, 134.8, 134.6, 134.2, 133.9, 131.4, 129.8, 129.7, 129.2, 128.9, 128.8, 128.1, 127.4, 127.2, 127.1, 126.3, 126.1, 125.9, 124.1, 123.6, 122.3, 121.3, 121.2, 120.4, 118.1, 117.9, 117.7, 117.2, 116.7, 116.4, 116.2, 111.7, 108.4, 20.4.

Synthesis Example 6

Synthesis of Compound 89

Compound 89 was synthesized through Reaction Scheme 6 below.

Reaction Scheme 6
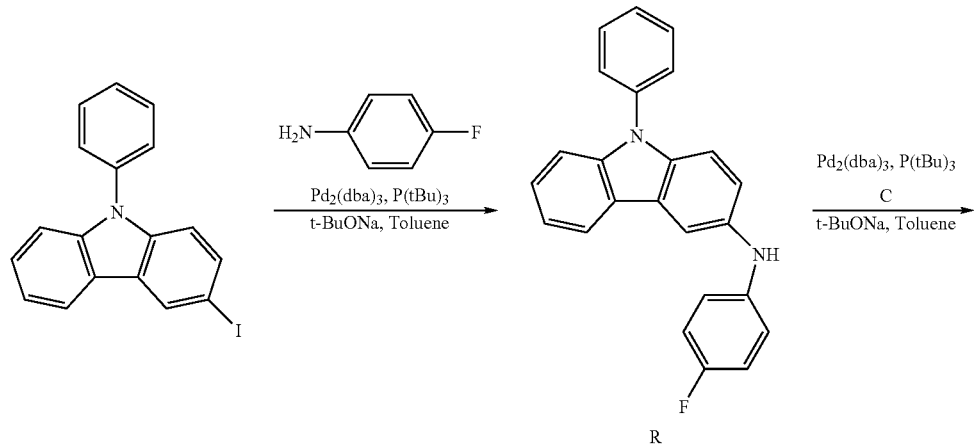
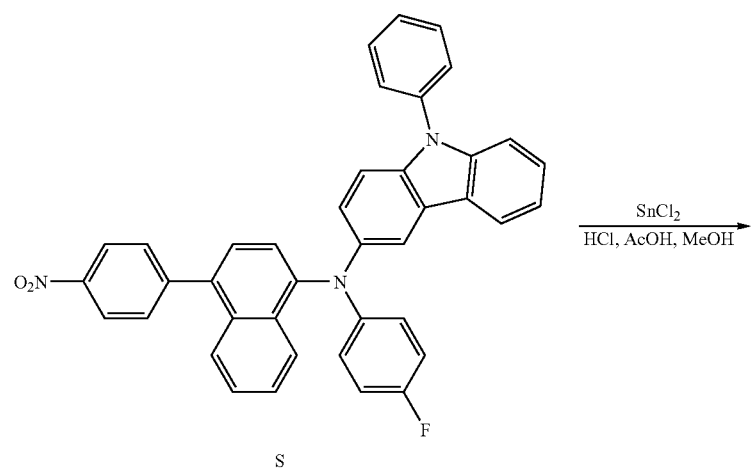
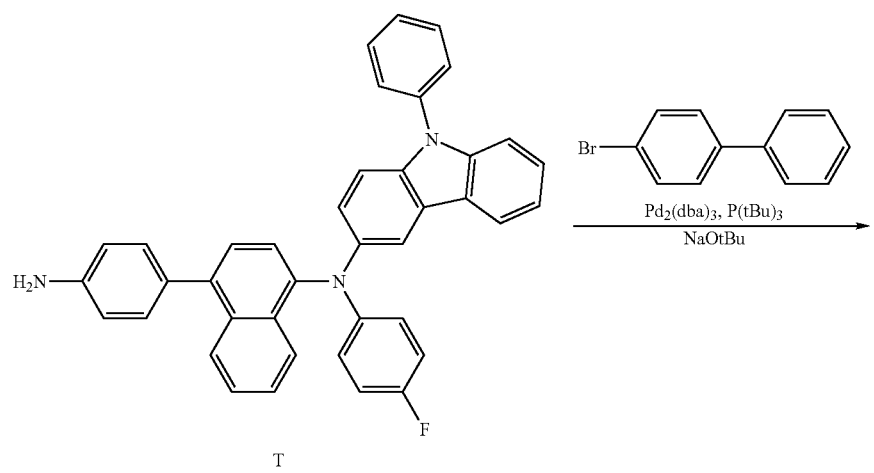

-continued

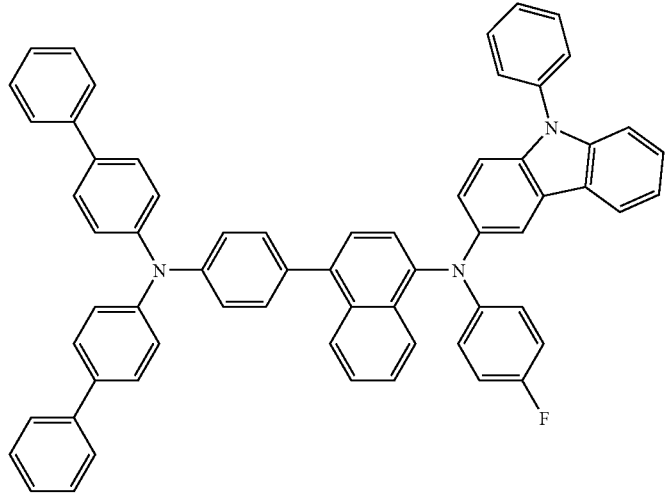

89

Synthesis of Intermediate R 3.69 g (10 mmol) of 9-phenyl-3-iodocarbazole, 1.67 g (15 mmol) of 4-fluoroaniline, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 3.17 g of Intermediate R (Yield: 90%).

$^1$H NMR ($CDCl_3$, 400 MHz) δ (ppm)—8.03-8.01 (m, 1H), 7.94 (d, 2H), 7.67 (d, 1H), 7.49 (d, 4H), 7.43 (d, 1H), 7.37-7.32 (m, 4H), 7.22-7.18 (m, 2H), 6.97-6.94 (dd, 1H), 5.68 (s, NH)

$^{13}$C NMR (CDCl3, 100 MHz) δ (ppm)—161.0, 157.8, 154.5, 140.7, 139.9, 137.4, 135.7, 129.8, 127.4, 127.1, 126.3, 119.1, 118.7, 118.5, 116.1, 113.1, 111.6, 111.2, 109.4, 102.5.

Synthesis of Intermediate S 3.28 g (10 mmol) of Intermediate C, 3.88 g (11 mmol) of Intermediate R, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 4.86 g of Intermediate S (Yield: 81%).

$^1$H NMR ($CDCl_3$, 400 MHz) δ (ppm)—8.10-8.06 (m, 3H), 7.93 (d, 1H), 7.68-7.59 (m, 4H), 7.54-7.31 (m, 14H), 7.10-7.05 (m, 2H), 6.76-6.73 (m, 2H)

$^{13}$C NMR (CDCl3, 100 MHz) δ (ppm)—162.0, 158.7, 155.5, 152.3, 149.8, 149.2, 145.1, 143.1, 137.9, 137.7, 136.4, 134.0, 132.7, 131.4, 129.8, 128.1, 127.4, 127.1, 126.3, 125.9, 124.7, 124.1, 123.9, 123.6, 122.3, 122.1, 120.4, 118.1, 117.7, 117.2, 116.7, 116.4, 116.2, 111.7, 108.4.

Synthesis of Intermediate T 6.0 g (10 mmol) of Intermediate S was dissolved in 20 mL of acetic acid and 10 mL of methyl alcohol. 189 mg (1 mmol) of $SnCl_2$ and a small amount of HCl were added thereto, and the mixture was stirred at 80° for 5 hours. After the reaction was completed, the mixture was cooled to room temperature and subjected to extraction 5 times using distilled water and 50 mL of diethyl ether. An organic layer was collected and dried using magnesium sulfate to evaporate the solvent. The residue was separately purified using silica gel column chromatography to obtain 4.78 g of Intermediate T (Yield: 84%).

$^1$H NMR ($CDCl_3$, 400 MHz) δ (ppm)—8.04 (d, 1H), 7.93 (d, 1H), 7.65-7.31 (m, 18H), 7.10-7.05 (m, 2H), 6.76-6.66 (m, 2H), 5.48 (s, $NH_2$)

$^{13}$C NMR (CDCl3, 100 MHz) δ (ppm)—162.0, 158.7, 155.5, 152.3, 149.2, 147.7, 145.1, 137.9, 137.7, 136.4, 135.4, 133.3, 132.0, 131.4, 129.8, 128.1, 127.4, 127.1, 126.3, 125.9, 125.7, 124.1, 123.6, 122.3, 120.4, 119.9, 118.1, 117.7, 117.2, 116.7, 116.4, 116.2, 115.6, 111.7, 108.4.

Synthesis of Compound 89

5.7 g (10 mmol) of Intermediate T, 2.56 g (11 mmol) of bromobiphenyl, 1.4 g (15 mmol) of t-BuONa, 0.18 g (0.2 mmol) of $Pd_2(dba)_3$, and 0.04 g (0.2 mmol) of $P(t-Bu)_3$ were dissolved in 40 mL of toluene, and the mixture was stirred at 90° for 3 hours. After the reaction was completed, the mixture was cooled to room temperature and subjected to extraction three times using distilled water and 40 mL of diethyl ether. An organic layer was collected and dried using magnesium sulfate to evaporate the solvent. The residue was separately purified using silica gel column chromatography to obtain 7.34 g of Compound 89 (Yield: 84%).

$^1$H NMR ($CDCl_3$, 400 MHz) δ (ppm)—8.21 (d, 1H), 7.93 (d, 1H), 7.75 (dd, 4H), 7.66-7.60 (m, 6H), 7.55-7.29 (m, 22H), 7.10-7.05 (m, 2H), 6.76-6.73 (m, 2H), 6.47-6.41 (m, 6H)

$^{13}$C NMR (CDCl3, 100 MHz) δ (ppm)—162.0, 158.7, 155.5, 152.3, 149.3, 149.2, 147.4, 145.1, 137.9, 137.7, 136.9, 136.4, 135.4, 134.8, 134.2, 133.9, 131.4, 129.8, 129.2, 128.9, 128.8, 128.1, 127.4, 127.2, 127.1, 126.3, 126.1, 125.9, 124.1, 123.6, 122.3, 121.3, 120.4, 118.1, 117.9, 117.7, 117.2, 116.7, 116.4, 116.2, 111.7, 108.4.

Example 1

A 15 Ω/cm² (1200 Å) ITO glass substrate, which was obtained from Corning Co. (Midland, Mich.), was cut to a size of 50 mm×50 mm×0.7 mm, microwave washed with isopropyl alcohol for 5 minutes, microwave washed with pure water for 5 minutes, and washed with UV ozone for 30 minutes. The glass substrate was installed in a deposition apparatus.

2-TNATA which is a known material was vacuum deposited on the substrate to form a HIL having a thickness of 600 Å, and Compound 8 according to the present embodiments was vacuum deposited on the HIL to form a HTL having a thickness of 300 Å.

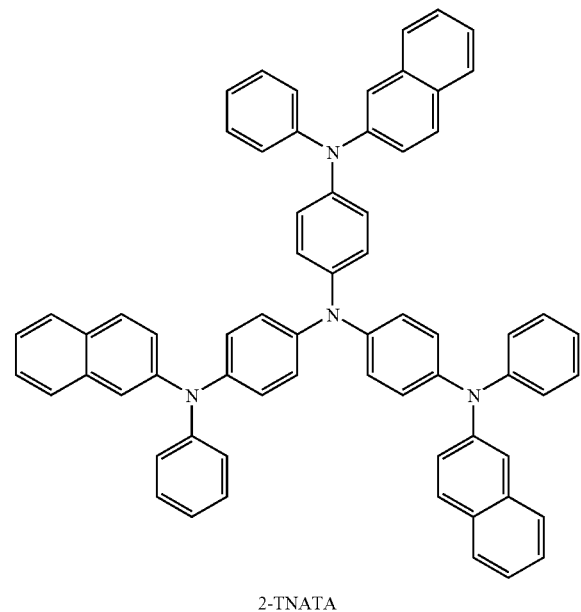

2-TNATA

IDE215 (Idemitsu Co.) as a known blue fluorescent host and IDE118 (Idemitsu Co.) as a known blue fluorescent dopant were co-deposited in a weight ratio of 98:2 on the HTL to form an EML having a thickness of 200 Å.

Then, $Alq_3$ was deposited on the EML to form an ETL having a thickness of 300 Å. LiF as a halogenated alkali metal was deposited on the ETL to form an EIL having a thickness of 10 Å. Then, Al was vacuum deposited on the EIL to form a cathode having a thickness of 3000 Å. In this way LiF/Al electrodes were formed, thereby completing an OLED.

A driving voltage of the OLED was 6.98 V, brightness was 8,846 $cd/m^2$, color coordinates were (0.144, 0.233), and efficiency was 8.85 cd/A at a current density of 100 $mA/cm^2$.

Example 2

An OLED was fabricated in the same manner as in Example 1, except that Compound 71 instead of Compound 8 was used to form the HTL.

A driving voltage of the OLED was 6.81 V, brightness was 8,861 $cd/m^2$, color coordinates were (0.146, 0.236), and efficiency was 8.86 cd/A at a current density of 100 $mA/cm^2$.

Example 3

An OLED was fabricated in the same manner as in Example 1, except that Compound 80 instead of Compound 8 was used to form the HTL.

A driving voltage of the OLED was 6.92 V, brightness was 8,471 $cd/m^2$, color coordinates were (0.145, 0.234), and efficiency was 8.47 cd/A at a current density of 100 $mA/cm^2$.

Example 4

An OLED was fabricated in the same manner as in Example 1, except that Compound 89 instead of Compound 8 was used to form the HTL.

A driving voltage of the OLED was 7.09 V, brightness was 8,370 $cd/m^2$, color coordinates were (0.144, 0.236), and efficiency was 8.37 cd/A at a current density of 100 $mA/cm^2$.

Comparative Example 1

An OLED was fabricated in the same manner as in Example 1, except that 4,4'-bis[N-(1-naphthyl)-N-phenylamino]biphenyl (NPB) which is a known material instead of Compound 8 was used to form the HTL.

A driving voltage of the OLED was 7.45 V, brightness was 6,102 $cd/m^2$, color coordinates were (0.144, 0.232), and efficiency was 6.1 cd/A at a current density of 100 $mA/cm^2$.

Figure 2:
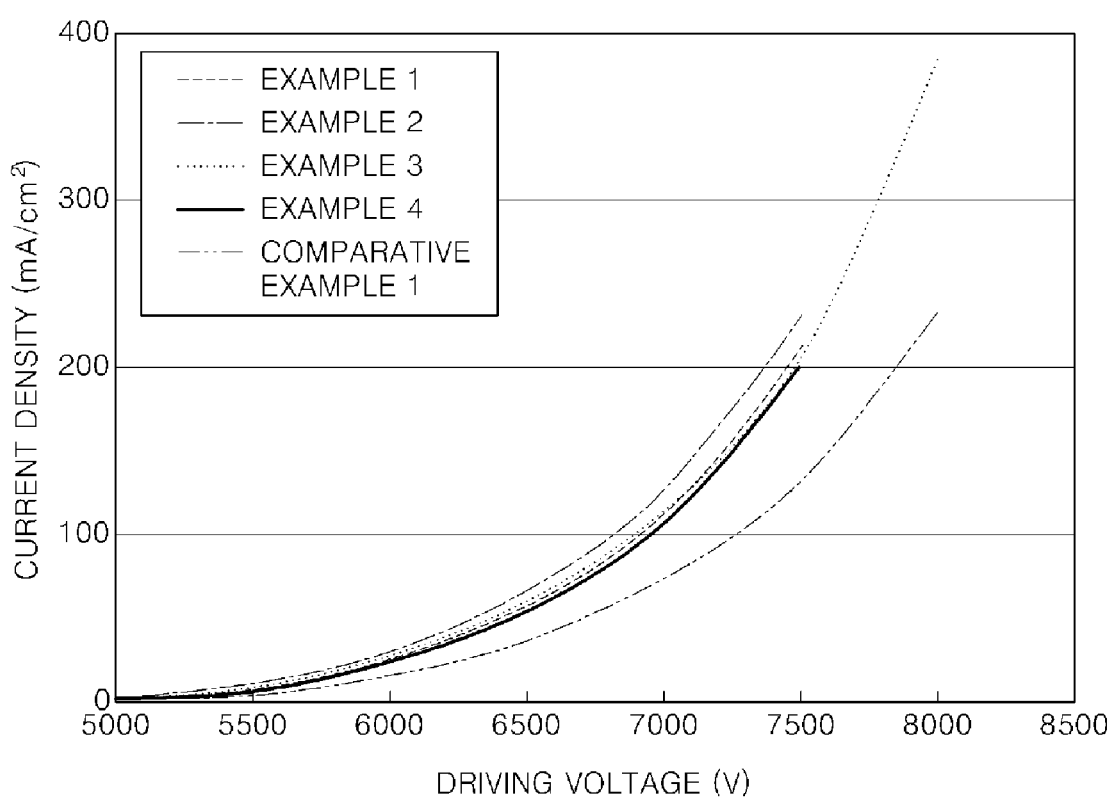
FIG. 2 shows a graph of current density characteristics of OLEDs according to an embodiment and conventional OLEDs.

As exemplified by the Examples detailed above, OLEDs fabricated using the compounds represented by Formula 1 or 2 according to the present embodiments as a hole transporting material have lower driving voltages and excellent I-V-L characteristics having significantly improved efficiency compared to OLEDs fabricated using NPB which is a known material (FIG. 2). The OLEDs according to the present embodiments have low driving voltage, high efficiency, excellent brightness, and long lifetime due to excellent hole injection and hole transport capabilities.

Since the compound represented by Formula 1 or 2 according to the present embodiments has excellent electrical properties and excellent charge transport capabilities, the compound can be efficiently used as a hole injecting material, a hole transporting material, and/or an emitting material which is suitable for a fluorescent or phosphorescent organic light emitting device (OLED) which can realize all colors such as red, green, blue, and white. Thus, an OLED including the compound can have high efficiency, high current density, low driving voltage, excellent brightness, and long lifetime.

While the present embodiments have been particularly shown and described with reference to exemplary embodiments thereof, it will be understood by those of ordinary skill in the art that various changes in form and details may be made therein without departing from the spirit and scope of the present embodiments as defined by the following claims.

What is claimed is:
1. A compound represented by Formula 1 or 2 below:

Formula 1

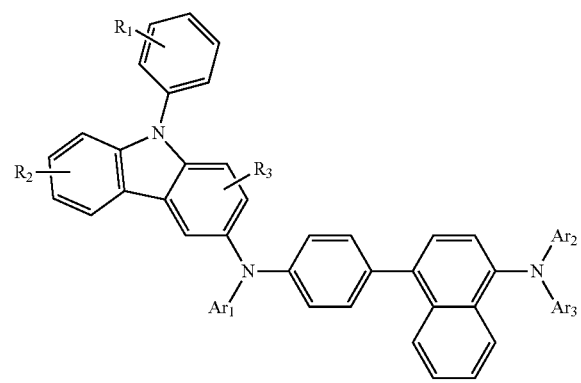

Formula 2

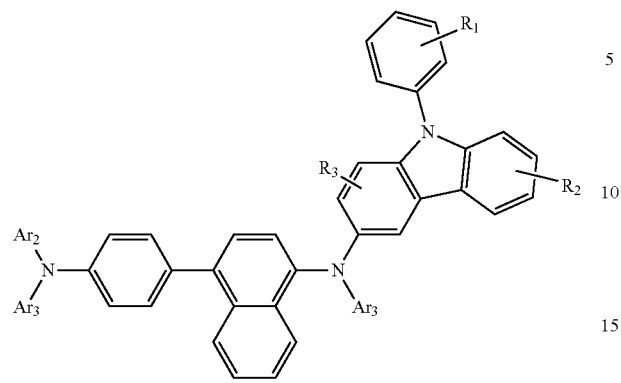

wherein Ar$_1$, Ar$_2$ and Ar$_3$ are each independently a substituted or unsubstituted C$_6$-C$_{20}$ aryl group, a substituted or unsubstituted C$_6$-C$_{20}$ aryloxy group, or a substituted or unsubstituted C$_4$-C$_{20}$ polycyclic condensed ring, and R$_1$, R$_2$ and R$_3$ are each independently a hydrogen atom, a substituted or unsubstituted C$_1$-C$_{10}$ alkyl group, a substituted or unsubstituted C$_1$-C$_{10}$ alkoxy group, a fluorine atom, a cyano group, or an amine group, wherein two or more of R$_1$, R$_2$, and R$_3$ can be bound with one another to form a saturated or unsaturated carbon ring.

2. The compound of claim 1, wherein Ar$_1$, Ar$_2$ and Ar$_3$ are each independently a phenyl group, a C$_1$-C$_5$ alkylphenyl group, a C$_1$-C$_5$ alkoxyphenyl group, a cyanophenyl group, a phenoxyphenyl group, a fluorophenyl group, a naphthyl group, a C$_1$-C$_5$ alkylnaphthyl group, a C$_1$-C$_5$ alkoxynaphthyl group, a cyanonaphthyl group, a halonaphthyl group, a fluorenyl group, a biphenyl group, a C$_1$-C$_5$ alkyl biphenyl group, or a C$_1$-C$_5$ alkoxy biphenyl group.

3. The compound of claim 1, wherein Ar$_1$, Ar$_2$ and Ar$_3$ are each independently a phenyl group, an ethyl phenyl group, an ethyl biphenyl group, an o-, m- or p-fluorophenyl group, a dichlorophenyl group, a dicyanophenyl group, a trifluorophenyl group, a methoxyphenyl group, an o-, m- or p-tolyl group, a mesityl group, a phenoxyphenyl group, an (α,α-dimethylbenzene)phenyl group, an (N,N'-dimethyl)aminophenyl group, an (N,N'-diphenyl)aminophenyl group, a pentalenyl group, a naphthyl group, a methyl naphthyl group, an anthracenyl group, an azulenyl group, a heptalenyl group, an acenaphthylenyl group, a fluorenyl group, an anthraquinolyl group, a phenanthryl group, a triphenylene group, a pentaphenyl group, or a hexaphenyl group.

4. The compound of claim 1, wherein Ar$_1$, Ar$_2$ and Ar$_3$ are each independently a monocyclic, bicyclic or tricyclic aryl group selected from the group consisting of a fluorenyl group, a phenyl group, a naphthyl group, a biphenyl group, and an aryl group having aromatic rings substituted with 1-3 substituents selected from the group consisting of a C$_1$-C$_4$ alkyl group, a C$_1$-C$_5$ alkoxy group, a cyano group, an amine group, a phenoxy group, a phenyl group and a halogen atom.

5. The compound of claim 1, wherein the compound is one compound selected from the group consisting of:

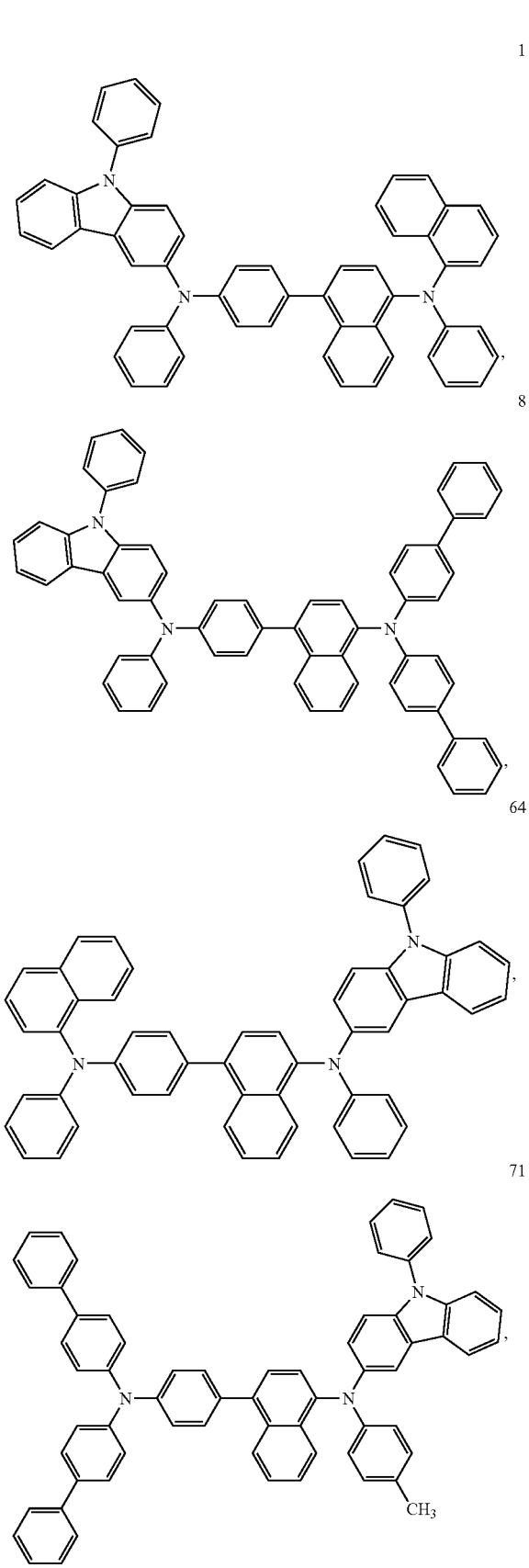

-continued

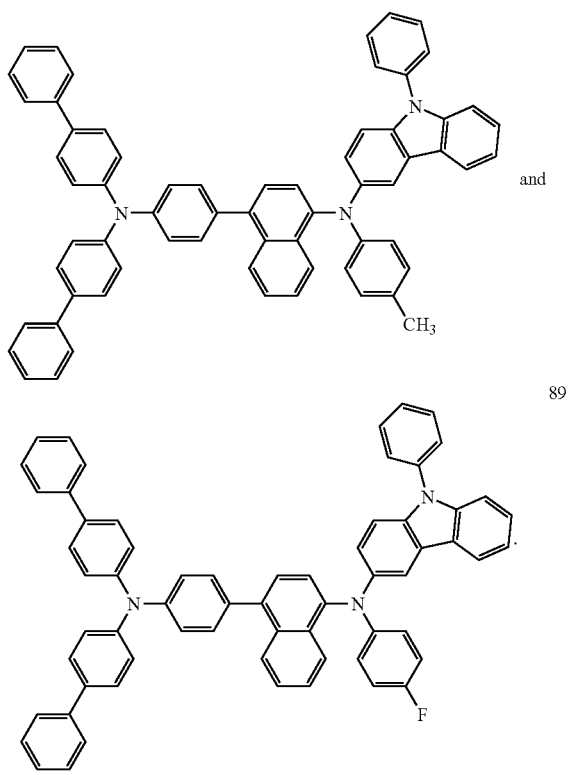

6. An organic light emitting device comprising
a first electrode;
a second electrode; and
an organic layer interposed between the first electrode and the second electrode,
wherein the organic layer comprises a compound according to claim 1.

7. An organic light emitting device comprising
a first electrode;
a second electrode; and
an organic layer interposed between the first electrode and the second electrode,
wherein the organic layer comprises a compound according to claim 2.

8. An organic light emitting device comprising
a first electrode;
a second electrode; and
an organic layer interposed between the first electrode and the second electrode,
wherein the organic layer comprises a compound according to claim 3.

9. An organic light emitting device comprising
a first electrode;
a second electrode; and
an organic layer interposed between the first electrode and the second electrode,
wherein the organic layer comprises a compound according to claim 4.

10. An organic light emitting device comprising
a first electrode;
a second electrode; and
an organic layer interposed between the first electrode and the second electrode,
wherein the organic layer comprises a compound according to claim 5.

11. The organic light emitting device of claim 6, wherein the organic layer is a hole injection layer or hole transport layer.

12. The organic light emitting device of claim 6, wherein the organic layer is a single layer having both hole injection and hole transport capabilities.

13. The organic light emitting device of claim 6, wherein the organic layer is an emission layer.

14. The organic light emitting device of claim 13, wherein the emission layer comprises the compound of claim 1 as a host and a phosphorescent or fluorescent dopant.

15. The organic light emitting device of claim 6, having a structure selected from the group consisting of a first electrode/hole injection layer/emission layer/second electrode structure, a first electrode/a hole injection layer/hole transport layer/emission layer/electron transport layer/second electrode structure, and a first electrode/hole injection layer/hole transport layer/emission layer/electron transport layer/electron injection layer/second electrode layer structure.

16. The organic light emitting device of claim 15, further comprising at least one layer of a hole blocking layer and an electron blocking layer.

17. A flat panel display device comprising an organic light emitting device of claim 6, wherein the first electrode of the organic light emitting device is electrically connected to a source electrode or a drain electrode of a thin film transistor.

18. A flat panel display device comprising an organic light emitting device of claim 11, wherein the first electrode of the organic light emitting device is electrically connected to a source electrode or a drain electrode of a thin film transistor.

19. A flat panel display device comprising an organic light emitting device of claim 12, wherein the first electrode of the organic light emitting device is electrically connected to a source electrode or a drain electrode of a thin film transistor.

20. A flat panel display device comprising an organic light emitting device of claim 13, wherein the first electrode of the organic light emitting device is electrically connected to a source electrode or a drain electrode of a thin film transistor.

21. A flat panel display device comprising an organic light emitting device of claim 14, wherein the first electrode of the organic light emitting device is electrically connected to a source electrode or a drain electrode of a thin film transistor.

22. A flat panel display device comprising an organic light emitting device of claim 15, wherein the first electrode of the organic light emitting device is electrically connected to a source electrode or a drain electrode of a thin film transistor.

23. A flat panel display device comprising an organic light emitting device of claim 16, wherein the first electrode of the organic light emitting device is electrically connected to a source electrode or a drain electrode of a thin film transistor.

* * * * *